(12) United States Patent
Hogue et al.

(10) Patent No.: US 11,798,689 B2
(45) Date of Patent: Oct. 24, 2023

(54) GENERATING CUSTOMIZABLE PERSONAL HEALTHCARE TREATMENT PLANS

(71) Applicant: Viviphi Ltd., Greenwood Village, CO (US)

(72) Inventors: Gerry Hogue, Englewood, CO (US); Fred Ashbury, Whitby (CA); Brian Leyland-Jones, Sioux Falls, SD (US)

(73) Assignee: VIECURE, Inc., Denver, CO (US)

( * ) Notice: Subject to any disclaimer, the term of this patent is extended or adjusted under 35 U.S.C. 154(b) by 1403 days.

(21) Appl. No.: 15/658,906

(22) Filed: Jul. 25, 2017

(65) Prior Publication Data

US 2018/0102190 A1    Apr. 12, 2018

Related U.S. Application Data

(60) Provisional application No. 62/366,226, filed on Jul. 25, 2016.

(51) Int. Cl.
| | |
|---|---|
| *G16H 50/70* | (2018.01) |
| *G16H 20/10* | (2018.01) |
| *G16H 50/20* | (2018.01) |
| *G16H 20/40* | (2018.01) |
| *G16H 10/60* | (2018.01) |

(52) U.S. Cl.
CPC ............ *G16H 50/70* (2018.01); *G16H 10/60* (2018.01); *G16H 20/10* (2018.01); *G16H 20/40* (2018.01); *G16H 50/20* (2018.01)

(58) Field of Classification Search
CPC ........ G16H 50/20; G16H 50/70; G16H 20/10; G16H 20/40; G16H 10/60
See application file for complete search history.

(56) References Cited

U.S. PATENT DOCUMENTS

| | | | |
|---|---|---|---|
| 2012/0231959 A1* | 9/2012 | Elton | G16H 50/80 435/6.12 |
| 2013/0197938 A1* | 8/2013 | Bayouk | G16H 10/60 705/3 |
| 2017/0083682 A1* | 3/2017 | McNutt | A61N 5/1038 |
| 2017/0116379 A1* | 4/2017 | Scott | G16H 50/20 |

* cited by examiner

*Primary Examiner* — Fonya M Long
*Assistant Examiner* — Anthony Balaj
(74) *Attorney, Agent, or Firm* — Holzer Patel Drennan

(57) ABSTRACT

Personalized treatment plan generation from an inference engine of a system. The system may receive or retrieve data from a plurality of sources and parse the data to generate individual data fields defining characteristics of a patient. The inference engine may process the contents of the individual data fields in relation to rule blocks suggesting certain treatment actions and combinations thereof in response to satisfied conditions. The inference engine may implement machine learning to refine rule blocks and improve functioning of the system to optimize healthcare.

17 Claims, 17 Drawing Sheets

FIG. 8

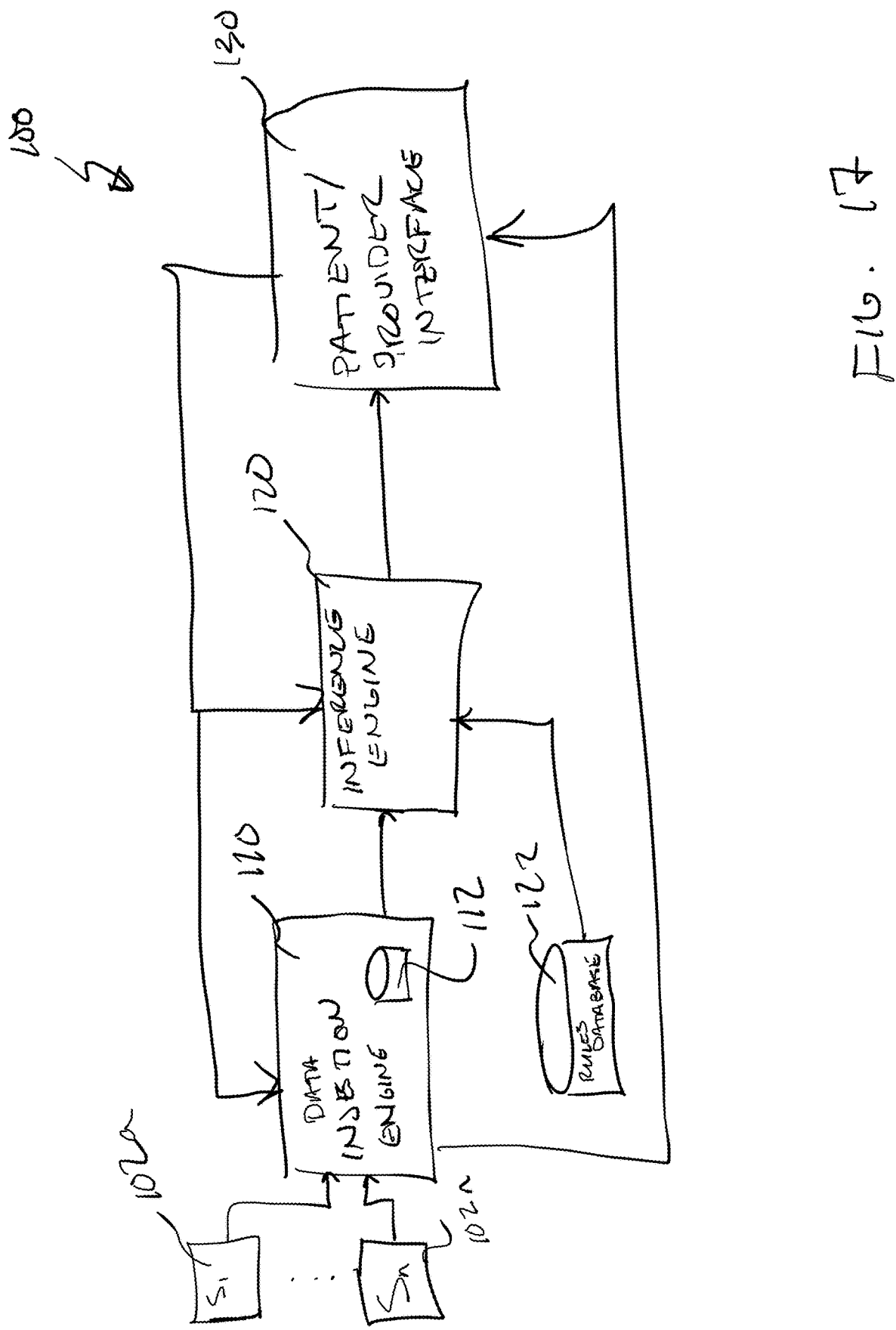

GENERATING CUSTOMIZABLE PERSONAL HEALTHCARE TREATMENT PLANS

RELATED APPLICATIONS

This application claims priority benefit of provisional U.S. Patent Application No. 62/366,226, filed Jul. 25, 2016, entitled "APPARATUS AND METHODOLOGIES FOR GENERATING CUSTOMIZABLE PERSONAL HEALTHCARE TREATMENT PLANS", the entirety of which is hereby incorporated by reference.

TECHNICAL FIELD

The present disclosure relates to medical treatment plans, and in particular to individualized treatment plans for use in treating cancer.

BACKGROUND

The delivery and management of healthcare to individual patients is becoming increasingly customized with more personal medical information and treatment options available than ever before. Difficulties in effectively providing customized healthcare can arise, however, where a provider or user needs to keep up-to-date with leading edge medical, biological, and environmental knowledge, and then needs to translate the vast amounts of knowledge to respond to the particular individual's healthcare needs successfully. Compounding this is the fact that individuals are often being treated by a team of medical professionals, spanning a variety of disciplines, that are rarely able to communicate with each other effectively. An additional complication is the fact that the same treatment may not be applicable to all, most or even a group of individuals, or it may impact individuals in different ways. In short, treatment of a medical condition is not a "one size fits all" proposition, especially in the context of complex medical disorder such as cancer. As a result, an individual with a specific diagnosis (e.g., cancer) is usually treated with standardized or conventional healthcare (e.g., chemotherapy, radiation therapy), which generally fails to be responsive to the genomic profile of the disease. Accordingly, the need persists for improvements for delivery and management of healthcare to individual patients.

SUMMARY

In view of the foregoing, there is a need for systems and methods of obtaining and analyzing information about an individual having one or more medical conditions to generate a personalized treatment plan. Generation of a personalized treatment plan may include continuously obtaining and interpreting the most current leading-edge knowledge, including genomic science, whether in the field of the one or more medical conditions or not, and extracting the relevant and pertinent knowledge based upon the individual's needs. It is desirable that such systems and methods may further comprise a feedback or learning component, personalizing selected treatment strategies and optimizing healthcare. It is further desirable that such a system may be entirely automatic, effectively creating a virtual health care team, to provide treatment considerations that are personalized to the individual, and that are better options than known standard of care.

The present disclosure includes sourcing information about an individual having one or more medical conditions. For instance, the individual may be suffering from a single, acute condition or a combination of conditions that may include diseases, disorders, or other medical issues. In short, the present disclosure relates to population and utilization of specific data structures that include data generated from sourced information about the individual. The data structure may include extracted or parsed data from the information about the individual. Specifically, the information about the individual may come from a variety of sources that may themselves be in different formats. For instance, digital files that include information about the individual may be processed to populate the data structure. Such digital files may include fields in proprietary, third-party formats, in standardized data files, or other formats. Additionally or alternatively, manually input data may be used to populate the data structure.

In addition, the present disclosure provides for extracting, according to clinical and scientific rules, relevant information from the data structure and generating, potentially at multiple points in time, personalized treatment plans for the individual. These rules may be stored in a rule data structure that stores a plurality of rule blocks (i.e., structured rules) with condition components and action components. The condition components may include rule attributes that correspond to individual data fields in the data structure. In turn, when operators are introduced into the rule, executable expressions that are based on the data populated in the individual data fields may govern the action of the rule. Notably, the terms "rule" and "rule block" may be used herein interchangeably.

As may be appreciated, rules may be generated or provided in a number of ways. For instance, manually derived rules may be provided in the rule data structure by a knowledge expert or the like. Further still, rules may be sourced from external sources. This external sourcing may include reformatting or translating a rule from a first form to a second form that conforms to the rule structure of the present disclosure. Further still, rules may be automatically generated by the system in response to analysis of outcomes of previous personalized treatment plans. That is, the rules may comprise a feedback component that allows outcomes to be provided quantitatively for evaluation, modification, and/or creation of rules for use in future applications based on the outcomes of prior personalized treatment plans.

In turn, the concepts provided by the present disclosure may effectively create a virtual health care team for the individual, the team being operative to automatically and continuously track and monitor the individual's health and optimize the personalized treatment plan. It is an advantage that the present disclosure may comprise a feedback learning component capable of adjusting and modifying the healthcare strategy based upon the individual's response to treatment, whether positive or negative. The learning component may further be used to predict one individual's response to treatment based upon the responses of other individuals to the same or similar treatment, further personalizing the individual's treatment and optimizing care.

In an embodiment, a system may be operative to receive or retrieve data from a plurality of sources including, but not limited to, electronic medical record (EMR) databases, clinic and hospital data systems, medical libraries, etc. Data received or retrieved may include patient structured data, patient genetic mutation data, rule sets (i.e., collections of rule blocks), treatment plan alternative data, etc. The system may also comprise a processing system and a storage medium. For instance, the system may comprise one or more data structures for storage of information about one or more individuals and/or rules. The data structure may include individual data fields that provide the information about the individual at a granular level. In turn, the individual data fields may be individually indexed for access by an inferencing engine that may retrieve and execute rules in relation to the individual data fields. That is, rules may be conditional upon specific information about the individual that is provided granularly in the individual data fields. In turn, the rules may provide specific analysis that is truly individual or personalized to the individual.

Sets of rule blocks may be stored within the storage medium and accessible by the inference engine operated by the processing system to scrutinize a patient's medical and health records (e.g., the individual data fields) to produce a recommended course of treatment for a medical condition. For example, the system may be particularly useful in analyzing a patient's genetic mutations to suggest a treatment regime corresponding to successful results of similar treatment therapies on the same or other patients. In this regard, the genetic data regarding the patient may be stored in the data structure. The genetic data may specifically be stored in a hierarchical data structure that allows for efficient and granular access to the genetic information of the patient (e.g., as input to a conditional component of a rule). In this regard, the personalized treatment plan may be conditioned on the specific genetic information of the patient.

In an aspect, a system and associated methodologies are provided for comprehensively obtaining up-to-date medical, biological, personal, environmental and other information about a patient to provide a cohesive treatment strategy for the patient at multiple points in time. Data related to a patient's continuity of care document (CCD) or consolidated clinical document architecture (CCDA) may be automatically retrieved or received over a data network from data sources such as CCD/CCDA extensible markup language (XML) documents, genetic screening data (Foundation One, Foundation ACT, Guardant), Health Level 7 (HL7) 2.x and Fast Healthcare Interoperability Resource (FHIR) interfaces, or any other available medical record storage format. As may be appreciated these sources may correspond to standardized formats and/or proprietary, third-party formats. Alternatively or additionally, data may be manually entered into the system via any common input device such as a keyboard or flash drive. Data files received in standard formats (e.g., CCD/CCDA, Genetic screening, HL7 2.x) may be inspected to determine what type(s) and/or format(s) of data are contained within the files. Inspection may include analyzing the data contained within a file to determine a standard file format that was used to create the file. Alternatively or additionally, inspection may comprise comparing the contents of a data file against a template of a known format to determine if the contents resemble the template, thereby indicating a known format. If the contents of the file do not resemble the template or are otherwise determined not to be of a particular format, additional comparisons may be performed, for example, the contents may be evaluated against additional templates. Upon making an initial determination as to the data type, a validation routine may be invoked to confirm the inspection results. A validation routine may, for example, involve a more thorough analysis of the data file contents. Once validated, a parsing routine corresponding to the identified file format may be invoked to process the data into individual data fields that are stored in a structured format in a database (i.e., patient structured data).

In another aspect, a CCD/CCDA XML file may be translated into a human readable format. Typically, data contained in the HL7 Standard CCD/CCDA XML file format is difficult to visually interpret. While many electronic medical record products produce this type of output file, there remains no simple method for rendering this type of file into a presentable human readable form that is readily comprehensible. Although doctors and other medical professionals may frequently interact with HL7 files, thereby gaining an understanding of their format over a period of time, many patients remain unfamiliar with the format and struggle to understand the contents.

By law, patients may ask their respective electronic medical record (EMR) vendor to provide them with a copy of their personal CCD/CCDA file, but patients and providers do not have a reliable and consistent method or system for viewing the contents in an easy to understand manner. Therefore, many patients may not be able to understand the contents of their EMR upon receiving a copy of it. Embodiments of the present invention remedy this problem by providing a method for transforming CCD/CCDA XML files into presentable hypertext markup language (HTML) that is comprehensible by both patients and healthcare providers alike.

In accordance with the present invention, CCD/CCDA XML files may be acquired manually or through an automated process. For example, a CCD/CCDA XML file may be acquired via an electronic interface or may be manually uploaded. Data from a CCD/CCDA XML file may be parsed into discrete values and stored in a logical and physical data schema constituting patient structured data. Such a schema may consist of saving the entire CCD/CCDA XML document as well as individual discrete parsed individual data fields organized into patient structured data. As described above, individual data fields may be discretely indexed for access and/or retrieval from the patient structured data. A custom extensible stylesheet language (XSL) stylesheet may be created to assist in rendering and transforming of the patient structured data into a readily understandable format. The patient structured data may be retrieved from the physical data schema and transformed into HTML for rendering to display via the aforementioned XSL stylesheet. The human readable CCD/CCDA HTML may then be displayed on a graphical user interface and/or hard-copy document for users to review.

In another aspect, a data structure and associated storage and retrieval method supporting storage of human gene mutation detail attributes may be provided. While many oncology EMR systems are capable of storing patient details, very few, if any, are capable of storing genetic mutation details at a level that allows them to be easily retrieved, analyzed and inspected for the purpose of decision making (e.g., serve as conditional attributes for evaluation in a rule). In accordance with an embodiment of the present invention, genetic sequencing data may be stored both as complete files and as parsed individual data points facilitating detailed analysis and decision making. Complete sequencing reports may be stored in the system in their entirety. Additionally, details may be parsed from files and stored in a hierarchical structure (i.e., patient genetic mutation data) that, like the patient structured data, may be granularly or individually indexed for access and/or retrieval (e.g., in the context of application of a rule).

Patient genetic mutation data may be retrieved by an inference engine and referenced in analyzing potential treatment options. Often, in traditional treatment methods, patient genetic mutation data may be unknown or overlooked by a treating physician. However, in accordance with the present invention, this data may be stored in a structure that allows for automated referencing by an inference engine to provide a treating physician with access to a volume of readily usable genetic mutation information that has traditionally been impracticable.

In another aspect, a data structure and associated storage and retrieval method supporting definition of rule blocks that facilitate treatment decision making may be provided. The method is operative for storing rule blocks for treatment recommendations. The rule blocks may comprise, inter alia, components, actions, groupings, and/or classifications. The rule blocks may be utilized by an inference engine to evaluate treatment recommendations utilizing patient structured data, patient genetic mutation data, and treatment plan alternative data (e.g., viable treatment options available for consideration).

A data structure associated with the method may be dynamic in that it can be customized to reference any and all data attributes present in the system (e.g., the data structure) to provide a comprehensive evaluation. Details associated with each rule block may be retrieved from the storage medium or a remote database and assembled into executable expressions. Executable expressions may be evaluated in real time using patient structured data and patient genetic mutation data. Rule blocks may each be comprised of condition-related components (dubbed "left hand side") and actions or recommendations (dubbed "right hand side"). A rule's left hand side may reference various data attributes which may or may not be stored in the system including, for example, specific genomic sequencing attributes. Left hand sides may combine multiple conditions or attributes with "and/or" conjunctions (among other potential operators) in order to increase specificity and variability of the rules.

A rule's right hand side may contain attributes detailing the actions to be carried out if and when the rule is evaluated to true (i.e., condition is satisfied). Actions may comprise or correspond to treatment plan alternative data. In other words, a rule block determined to be "true" may define an action including a treatment therapy that is identified by treatment plan alternative data which may be received or retrieved from an external database or may be manually entered by a user. Further still, a rule block may include all rules from a rules data structure that includes conditional components based on rule attributes associated with corresponding individual data fields in the patient structure data (e.g., including the patient genetic mutation data). In turn, all rules may be retrieved for which there is populated data in the individual data fields. As may be appreciated, certain retrieved rules may include conditional components that are based on individual data fields that are not populated for a given individual. In such, instances, "backward" operation of the rules may allow for generation of a query for individual data fields that are missing, but needed for evaluation of a rule.

In another aspect, a data structure and associated storage and retrieval method supporting definition of a patient treatment plan may be provided. Treatment plan alternative data associated with a patient treatment plan may consist of various content elements including: drugs, labs and tests, assessments, radiation, visits, surgery, and other interventions that may be recommended to a treating physician or other user based upon "true" and "false" indications given by rule blocks.

Individual content items within treatment plan alternative data may be codified with respective medical vocabularies or lexicons including:
- Logical Observation Identifiers Names and Codes (LOINC) for LABS/Test
- Common Terminology Criteria for Adverse Events (CTCAE) Grading Scheme toxicities
- National Drug Code (NDC) identifier information
- Systematized Nomenclature of Medicine (SNOMED) Codes
- International Classification of Diseases (ICD) 10 Codes Content items may be stored in respective event structures to identify when items are to be scheduled within the treatment plan. Cycle event items may be stored in respective date tables in order to manage actual scheduled dates. Cycle event date structures may be analyzed to determine additions, deletions, and modifications to the proposed treatment plan.

In an aspect, a goal and treatment intervention driven inference engine for analysis of patient related data to generate a suggested treatment plan may be provided. A network of computer-implement processes may be invoked to execute the functionalities of an inference engine described herein. A method implemented using an inference engine may be operable to analyze patient structured data (e.g., including patient genetic mutation data). The method may include analyzing patient structured data including but not limited to demographics, diagnostics, lab and test results, medications, and social history, as well as patient genetic mutation data that provide information relevant to treatment interventions suggested in accordance with treatment plan alternative data. An inference engine may receive the data for given patient(s) and process rule blocks. Treatment intervention options may be derived in accordance with the processing of the inference engine utilizing treatment plan alternative data. Treatment intervention options may then be presented to users via a graphical user interface (GUI). Interventions may be selected for inclusion in a patient specific personalized treatment plan.

Patient structured data may be retrieved from the storage medium to generate a patient avatar (i.e., a digital model representative of characteristics of the patient). Defined structured rule sets comprising rule blocks may be retrieved from the storage medium or an external database. Rule sets may be compiled into executable expressions. A classification rule set may be initially executed to determine additional applicable rule set(s) that should be executed based upon contents of the patient related data as described above. In this regard, a classification rule set may be invoked to analyze the structured data in the storage medium to identify which individual fields are present in the parsed data. Based upon the pool of individual fields that are identified, the appropriate rule blocks may be selected for application to the data by the inference engine. In other words, rule blocks containing attributes which correspond to the identified individual fields in the structured data may be selected for use by the inference engine.

All rule blocks in a selected rule set, or a subset thereof, may be evaluated against the patient avatar until all rule blocks in the selected set(s) have been processed. Based upon results of the evaluation, a database for additional rule blocks may be queried and evaluated. That is, certain conditional components of rules may be conditional on the outcome of a previously evaluated rule, such that rules may be hierarchical and/or cascading. Remaining rule blocks (if any) may be evaluated against the patient avatar.

The inferencing process may be initiated via multiple access points including:

Creating a new personalized treatment plan

Opening an existing personalized treatment plan

Inferencing via representational state transfer (REST) application programming interface (API)

Inferencing via internal testing tools

Once initiated, rule blocks may be retrieved from the rule sets. Individual rule blocks may be analyzed and, based on the attributes they reference, various methods may be employed to devise a compiled rule that can be evaluated. The methods employed may include but are not limited to:

determining if a patient has a particular gene mutation by name; and determining if a patient gene mutation contains specific gene attributes as identified.

The inference engine may evaluate a rule block using standard boolean operators (e.g., <, >, <=, >=, !=, etc.). The inference engine may evaluate presence or non-presence of a value or range of values. The inference engine may evaluate counts, and counts of collections of attributes. The inference engine may evaluate attributes based on a reference in time i.e., start and end date inclusive. The inference engine may evaluate numerical values utilizing modifiers and/or statistical functions including:

nadir or minimums;

zenith or maximums;

average;

standard deviations;

percent change;

absolute change (e.g. real numbers);

null versus empty value versus zero value;

linear equations to identify trending; or other known mathematical and statistical functions.

Rule block attributes may be inspected and compiled into executable algorithms. The compiled rule blocks may be evaluated against the patient avatar. The inference engine may track and log the result of each evaluation, retaining status so that it may identify which rule blocks evaluate to "true" and which rule blocks evaluate to "false." Rule blocks may be structured into tiers such that lower tier rule blocks evaluate input data (e.g., patient structured data, patient genetic mutation data, treatment plan alternative data, etc.) whereas upper tier rule blocks may evaluate results of lower tier rule blocks. In other words, the left hand side of an upper tier rule block may assess the right hand side or true/false result of lower tier rule blocks.

Inferencing may repeat iteratively until all applicable rule blocks have been evaluated. Logged "true" rule block evaluations may be assessed for conflicts (e.g., by executing an additional tier of rule blocks) and a final treatment recommendation list may be prepared. The recommendation list may be returned to the user for display in the GUI or as raw data for consumers utilizing a REST API. Recommendations may be displayed in the graphical user interface as selectable items. The recommendations may be strongly typed and codified so that they may be included in a personalized treatment plan.

In another aspect, a method for rendering a historical timeline representation of a patient's medical history may be provided. The method may be utilized to render a patient's medical history (e.g., including patient structured data) into a graphical timeline. While EMR vendors use various techniques to display patient history, this method generates an easy to understand timeline-style diagram that provides an efficient means of reviewing a patient's medical history.

The initial data for the timeline may be acquired via CCD/CCDA XML file parsing or manual entry. Historical data items may be categorized into one or more categories. Categories may include, for example: diagnosis, imaging, drug, surgery, radiation, genetics/genomics, laboratory/pathology results, or regimen, among other possible categories. Bounding dates (e.g., including high and/or low values) may be computed as historical data items are retrieved or received or sometime thereafter. In this regard, the earliest and latest dates associated with the pool of data may be determined to establish a period of time associated with the limits of the timeline. A timeline may then be graphically rendered with the aforementioned categories and bounding dates to present an interactive overview of a patient's medical history.

Each retrieved patient historical data item may be rendered into an appropriate timeline categorical portion. For instance, each categorical portion may be assigned a given row in the timeline separate from other categorical portions. The timeline may allow historical data items to be edited by a user to edit attributes (e.g., start date, end date, description, and category). Additionally or alternatively, a user may be able to select an option to initiate a download or rendering of input data files (e.g., CCD/CCDA XML file) associated with the timeline entry.

In another aspect, a method for rendering a grid representative of a comprehensive patient treatment plan for creating or editing a personalized treatment plan may be provided. Historically, it has been very difficult to craft a detailed patient treatment plan. This activity has traditionally been carried out manually on paper and has been prone to errors, oversights, and safety issues. For example, incorrect scheduling, drug dosing, and drug to drug interaction conflicts are prevalent in traditional methods. The described method is operative to outline a graphical user interface that addresses the aforementioned issues by providing a systematic grid-based approach to crafting a detailed and thorough plan of care (i.e., personalized treatment plan).

Treatment planning components may be dragged and dropped and/or double-clicked to add them to the graphical representation of the personalized treatment plan. As the personalized treatment plan is populated with treatment planning components, treatment plan grid items may be grouped by type, for example, visits, agents/actions, radiation, tests, surgeries, assessments, or toxicities. Individual grid cells may represent scheduling of a given item within the confines of a treatment plan phase, cycle, and/or day, etc. In other words a first axis may define a time-related constraint (e.g., third day of patient's treatment) and a second axis may define treatment options (e.g., radiation).

Treatment recommendations in accordance with treatment plan alternative data for inference engine processing may be provided for drag and drop operations or other means of selection. Alternatively, pop-up windows or other visual indications alerting a user to suggested treatment options may be generated based upon inferencing. Individual rows of the grid may be edited via a pop up editing screen which allows for users to provide additional details. Individual cells may be edited, for example, to schedule or unschedule an item, specify dosages, etc. As drug interventions are added to the plan, real time drug interaction checking may occur using the inference engine resulting in an alert being provided to a user if any potential hazards are detected. Additionally, as drug interventions are added to the plan, the inference engine may determine monitoring tests and toxicity assessments are necessary, based upon rule blocks, and these actions may be automatically added to the personalized treatment plan. Users may switch to other views of the personalized treatment plan, for example phases by clicking the appropriate button(s).

In yet another aspect, a method for creating an electronic document representing a comprehensive clinical trial quality patient treatment plan may be provided. Traditionally, the documentation of treatment care plans has been a pen and paper process which may yield omission of critical details or other errors. The method described herein provides for automated generation of a "clinical trial quality" treatment plan document.

A clinical trial quality treatment plan document may contain all pertinent personalized treatment plan details. The first page may contain a summary outlining the entire personalized treatment plan. The personalized treatment plan document may contain scheduling details for each phase, cycle, and day of the patient's personalized treatment plan. Additionally, a personalized treatment plan document may outline all interventions present in the personalized treatment plan including but not limited to: drugs/agents, lab tests and results, assessments, radiation treatment details, surgery details, etc.

A personalized treatment plan document may outline treatment management rules, eligible clinical trials, frequently asked questions, etc. and may include a toxicity grading scheme/scale, treatment team contact and emergency information, drug monographs and therapy administration instructions for all drugs included in plan, a complete patient summary, etc. Although it is envisaged that a clinical trial quality treatment plan document may be created in hard-copy or digitally, in a preferred embodiment such a document may be saved in PDF format such that it can be easily printed and transmitted electronically via HL7 MDM or XDS.B Document interfaces.

In another aspect, a method for identifying patient treatment plan shortcomings, errors, and holes in coverage may be provided. The method may be operable to address the problem of missing tests, assessments, and treatment management rules that could adversely affect patient treatment if not recognized.

Utilizing treatment plan alternative data, various treatment plan components may be analyzed for shortcomings, errors, and holes in coverage. Treatment plan drugs may be retrieved and analyzed to determine all applicable monitoring laboratory tests and toxicity assessments. Treatment plan test content present in the plan may be analyzed and compared to list of applicable monitoring laboratory tests such that any holes, deficiencies, short comings or missing tests may be identified and reported back to a user via a graphical user interface or printed treatment plan report. Treatment plan toxicity content present in the plan may also be analyzed and compared to a list of applicable monitoring toxicity assessments. Any holes, deficiencies, shortcomings or missing toxicity assessments may then be identified and reported back to a user via a graphical user interface or printed treatment plan report. Similarly, treatment management rule content present in the plan may be analyzed to determine if any applicable management rules are missing from the plan, e.g., testing a red blood count.

In accordance with this aspect, an existing patient treatment plan (e.g., a manually generated plan) may be uploaded or other obtained and evaluated. Evaluation of the patient treatment plan may include accessing rule blocks to perform an assessment of the patient treatment plan to identify treatment options which have been selected by a medical provider but which are inconsistent with right hand side results of one or more rule blocks. In this regard, the system may be utilized as a means of obtaining a "second opinion" to confirm or call into question a suggested patient treatment plan.

BRIEF DESCRIPTION OF THE FIGURES

Figure 8:
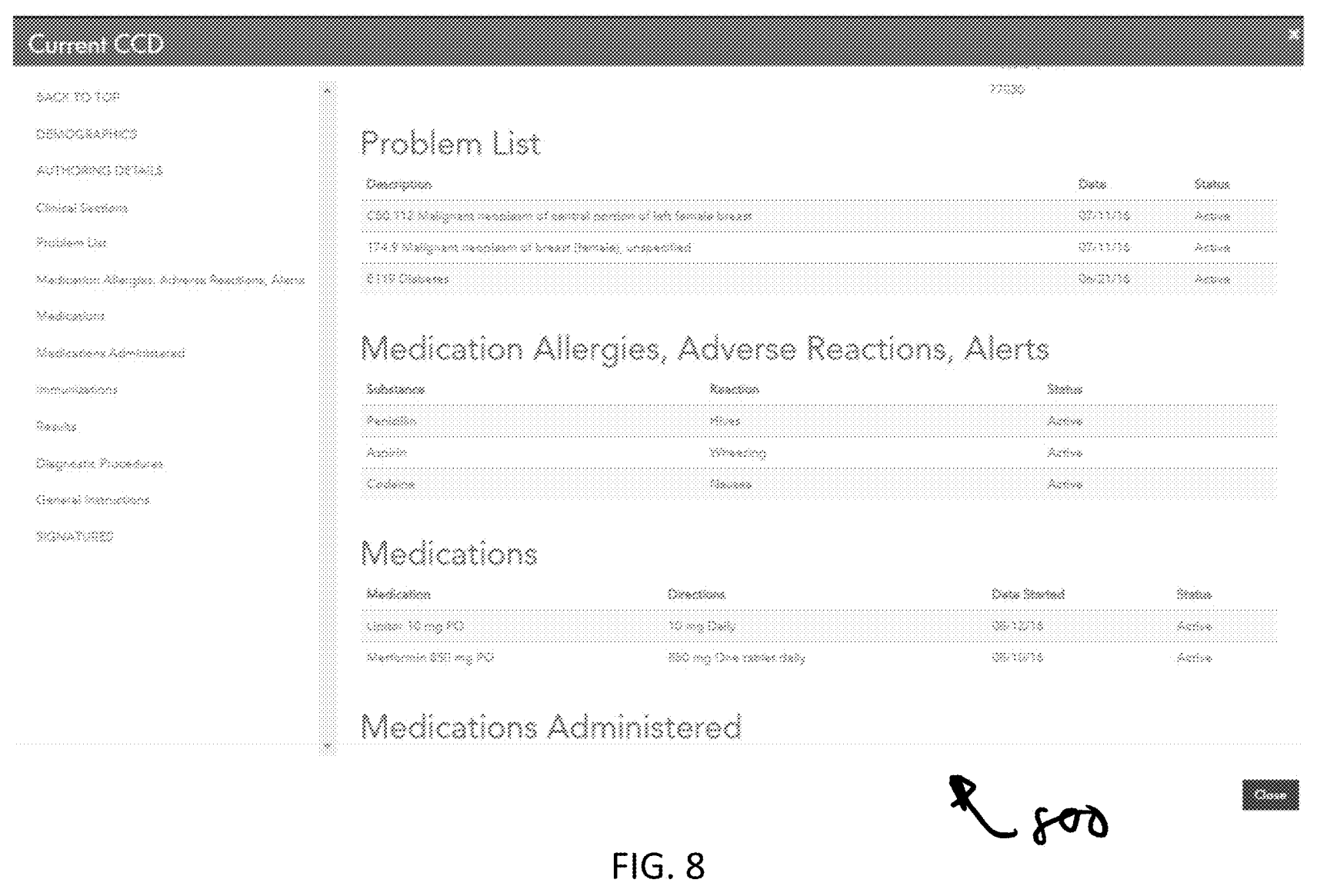

FIG. 8 illustrates an embodiment of a graphical user interface for patient data output.

FIG. 17 illustrates an embodiment of a system for use in generation of a personalized treatment plan.

DETAILED DESCRIPTION

Figure 1:
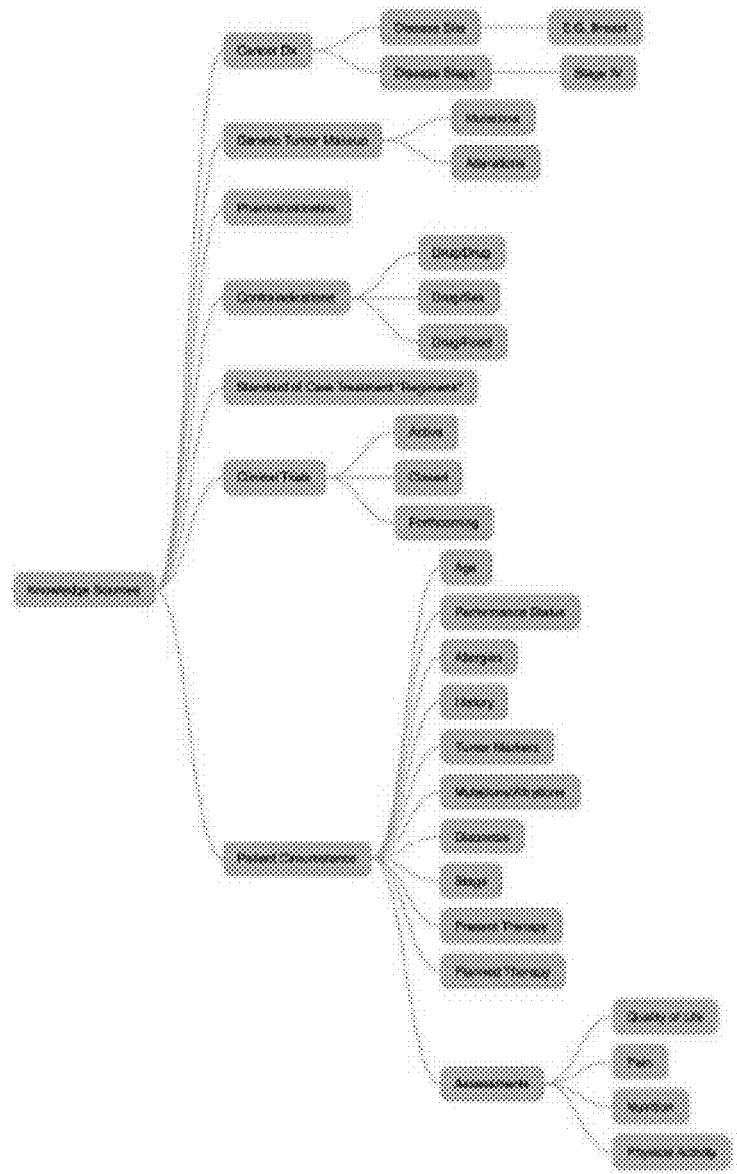
FIG. 1 is an exemplary model illustrating the relationships between various sources of data and their content.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

With regard to FIG. 1, a system and associated methods described herein may comprise a knowledge sourcing step comprising, for example, the sourcing of medical, biological, and molecular knowledge, information and data about the individual from a variety of sources, such as, without limitation, the disease site and stage, genetic alterations, including mutations and amplifications, pharmacokinetics, specific contraindications (i.e., based upon the individual's current care), and known standard of care regimens. In addition, the system and associated methods may incorporate current and up-to-date scientific information (e.g., from ongoing clinical trials), not only to personalize the individual's treatment, but to determine whether or not the individual may, for example, be a candidate for new experimental treatments or clinical trials. A system and associated methods may also incorporate specific personal information about the individual, which may or may not directly relate to the individual's one or more disorders. For example, the individual's age, performance status on certain treatments compared to others, allergies, family history, previous healthcare and/or treatment history, lifestyle factors (e.g., smoking, diet, physical activity, or alcohol consumption), biomarkers, genetic alterations, including mutations and amplifications, previous and current medical diagnoses, the stage of any such disorders, and current and/or planned treatment of any such disorders. In addition, a system and associated methods may assess or predict the individual's treatment outcome, incorporating and interpreting information about the individual's quality of life, their pain, nutritional habits or difficulties, and physical activity limitations.

Figure 2:
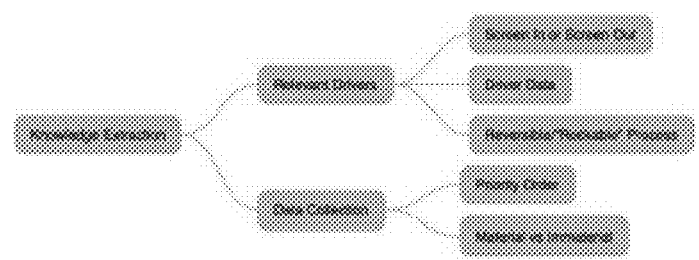
FIG. 2 is an exemplary model illustrating the extraction of knowledge from various sources of data.

With regard to FIG. 2, methods described herein may then comprise a step of extracting relevant information from the sourced knowledge (e.g., patient structured data, patient genetic mutation data, treatment plan alternative data, and/or rule blocks) to specifically apply the appropriate sourced knowledge, thereby applying the information across several categories to synthesize leading-edge scientific and clinical knowledge for personalized treatment at a particular point in time. By way of example, a system may source knowledge, information and data pertaining to cancer including, inter alia, primary and secondary disease sites, disease stage, genetic pathway and tumor makeup highlighting genetic alterations (mutations, deletions, insertions and amplifications) in the tumor and healthy tissue, various interventions, pharmacokinetics, contraindications, clinical trials, and the individual's lifestyle and circumstances. It is understood the foregoing knowledge, information and data may be collected manually, automatically, or in combination thereof.

More specifically, methods described herein may include extractions of the relevant scientific and clinical knowledge, information and data to assess and interpret the information, using clinical and scientific rules, and utilize the extracted information to provide a personalized treatment plan. Knowledge, information, and data for cancer diagnosis may include patient structured data, patient genetic mutation data, and treatment plan alternative data such as:

primary and secondary disease sites (e.g. breast, lung, colon, etc.);
disease stage (the size, aggressiveness, and progression of the disease);
genetic pathway and tumor makeup highlighting genetic alterations (mutations, deletions, insertions) in the tumor and healthy tissue (DNA, RNA, Proteins);
interventions such as anti-hormonal therapies, immunotherapies, and targeted therapies regardless of whether they are approved for use in the primary disease site and/or cancer stage (including experimental interventions and interventions that are, or should be on a molecular basis, effective on a specific gene/pathway);
pharmacokinetics knowledge about how the intervention will interact and/or reacts in the body including how the intervention will move into, throughout, and back out of the body, and the time course of its absorption, bioavailability, distribution, metabolism, and excretion, knowledge about what an intervention does to the body, how it involves receptor binding, its post receptor effects, and known and/or expected chemical interactions to determine the onset, duration, and intensity of an intervention's effect;
contraindications of interventions and/or drugs including but not limited to drug/drug, drug/sex and drug/food contraindications;
standard of care treatment "regimens" that are multi-disciplinary in nature such as surgery, radiation therapy, chemotherapy, anti-hormonal therapy, immunotherapy and targeted therapy, dose, schedule, route, management rules, toxicity measures, supportive care, diagnostic tests, interpretation knowledge and the like;
clinical trials the patients' circumstances may make them eligible for and/or innovative therapies including those that are active, recently closed or forthcoming; and
patient circumstances including age, performance status (ability to withstand various treatments based on strength, ability to conduct day-to-day chores, etc.), allergies, disease history including prior treatments, tumor markers, genetic makeup of tumor including any driver and ancillary genomic alterations, confirmed pathological and clinical diagnoses and stage of disease, present therapies the patient is enrolled in, planned therapies/interventions and various critical assessments such as quality of life, pain management, nutritional situation and physical activity behavior.

The knowledge extraction can, inter alia, screen potential interventions in or out in terms of applicability, eligibility and efficacy, determine driver data, what (if any) data are missing and what is the optimal way/sequence to collect the data, and sequence and structure the "logic" sets to optimize collection of missing/needed data to include potential therapies as viable candidates or exclude them from consideration. It is an advantage of the present system and associated methods that such extraction may be performed in a manner to operate in a forward-like manner, determining a solution (e.g., treatment) based upon presented data, and/or in a reverse-like manner, determining needed data/characteristics (e.g., patient structured data) in order to confirm a solution set as viable for the situation. Alternation between forward and reverse-modes may occur by intelligently switching or "rocking" from forward to reverse and back in order to optimize the time and data collection needed to arrive at candidate solutions. The present knowledge extraction may further determine specific data collection strategies and processes needed to optimize the priority and sequence of data collection, and to rank and optimize data collection in terms of material versus less material sourced knowledge, information and data.

Figure 3:
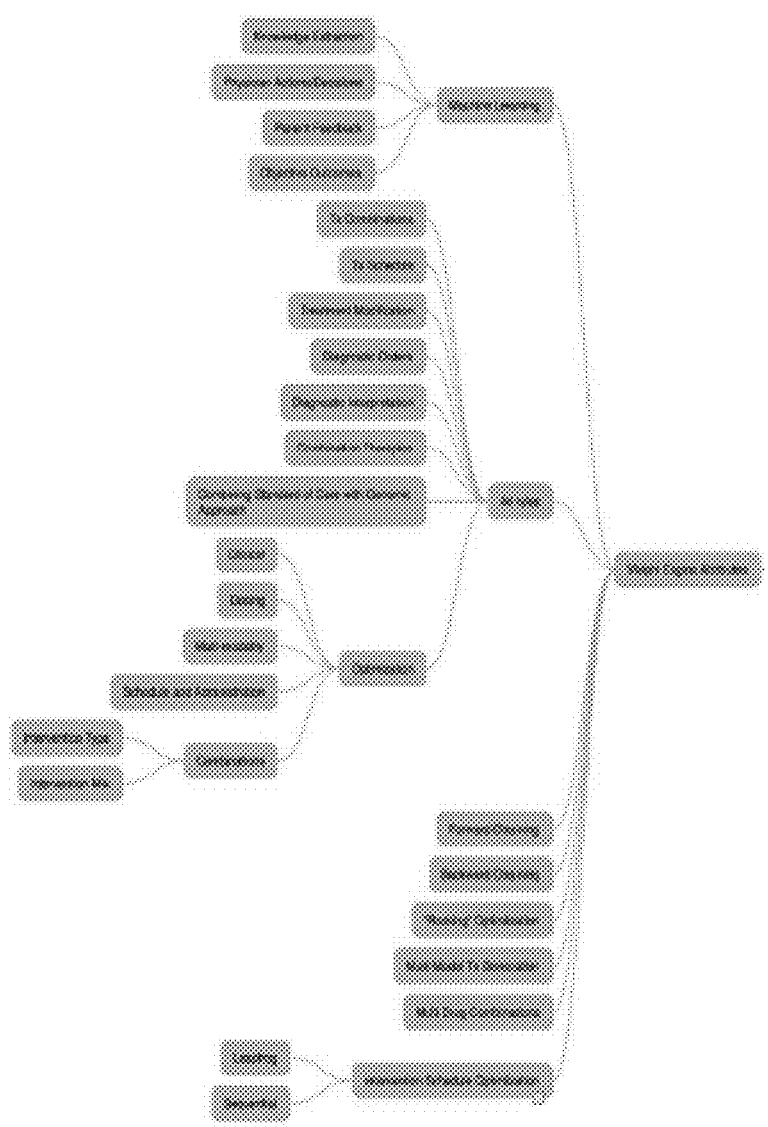
FIG. 3 is an exemplary model illustrating the relationship between various inference engine attributes.

With regard to FIG. 3, once the scientific and clinical knowledge, information and data has been sourced and appropriately extracted, a system and associated methods are operative to automatically, over time, perform the step of generating personalized treatment considerations (i.e., a personalized treatment plan) for the individual to optimize outcomes. This step is performed by a processor operative to apply knowledge, reason and evidence from the extracted knowledge base and the individual's data attributes. According to embodiments herein, a system may be operative to perform machine learning with respect to knowledge extraction, knowledge application and results-based learning, artificial intelligence (AI) application, methods of AI engine application, such as direction of knowledge processing and combination therapy generation directed by genomic science based on theoretical benefit of applying scientific facts and attributes of individual therapies in a combinatorial manner, and intervention and schedule optimization.

More specifically, machine learning may comprise automated learning and adaptation of the knowledge base by, at least, monitoring trends, contends and advances identified, extracted and/or gleaned from scientific peer-reviewed publications, private discoveries by world-leading authorities on subject matter (e.g., discoveries made by leading cancer researchers) and other approved scientific and clinical knowledge resources. The knowledge extraction process may comprise automated indication of new advances, more robust combination therapies based on the science inherent in yet uncombined components (e.g., a drug that is effective on the ALK mutation in lung cancer being effective on an ALK mutation in colon cancer) based on the science of how it binds to a specific molecule to prevent binding with other molecules. The monitoring and learning process may comprise automated physician or expert user modifications and/or endorsement and use of engine generated considerations based on the actions and decisions, as recommended in accordance with rule blocks, the experts ultimately take. Monitoring may further automate direct patient feedback in relation to the benefit/outcome expected from the intervention. Finally, the machine learning may comprise the determination of objective outcome data and information (e.g., 45% of a statistically valid sample of patients experienced complete remission when standard of care expected to achieve 1% complete remission for a specific late stage group of patients).

An AI engine (which may be the same as or different than the Inference Engine) may dynamically consider various constructs for innovative therapies. More specifically, the AI engine may consider treatment combinations (e.g., combining radiation therapy, chemotherapy backbone with anti-hormonal, immunotherapy and targeted therapy based on the individual's disease, state, performance status, tumor markers and genetic alterations). The AI engine may further consider treatment scheduling to automatically sequence and schedule interventions, preventing conflict with combinations created by the engine, taking into account multiple variants and combinations by, for example, applying pharmacokinetic knowledge related to activation and elimination. The AI engine may perform dynamic treatment modification (i.e., revisions to a personalized treatment plan) based upon diagnostic test results and documented experimentation of multi-modality combination therapies (e.g., 50% starting dose when combined with another intervention that conflicts with metabolizing the other agent/intervention administration). The AI engine may consider diagnostic orders that are scientifically and/or clinically indicated for the safe monitoring of intervention administration by formatting them into rule blocks. The AI engine may further consider diagnostic interpretation of patient response indicators and test results present in patient structured data, subsequently modifying personalized treatment plan details such as dose, schedule etc., and the combination or modification of standard of care treatment regimens to reflect additional interventions based on a genomic approach (e.g., adding a targeted therapy because the patient has lung cancer and the ALK mutation). Finally, the AI engine may utilize rule blocks to consider optimization of the numerous combinations based upon safety and efficacy related to clinical practice, dosing ranges and escalation/reduction/omission requirements based on management knowledge for the interventions used, multi-modality schedule and administration considering intervention type and mix (e.g., radiation therapy, chemotherapy, and targeted therapy). The AI engine may modify rule blocks iteratively as new input data is received.

Broadly, with further regard to FIG. 3, the present AI engine may perform knowledge application by modifying right hand side recommendations including combinatory and iterative application of forward and backward processing ("chaining"), "rocking" optimization (continuously reversing and/or suspending chaining to solicit and/or process knowledge and real time data provision to refine the solution set where needed), combining multi-modes of therapy in optimal known and theoretical best sequence (e.g., neo-adjuvant targeted and immunotherapy in advance of ovarian cancer surgery to shrink the tumor and combat mutations floating in the blood stream post-surgery), combining multiple drug interventions and simultaneous therapies (triples, quads, etc.), and optimizing the schedule of all the foregoing in order to maximize the power of simultaneous versus sequential interventions (e.g., leapfrog or staged schedule for conflicting drugs; giving one drug while ceasing another).

Figure 4:
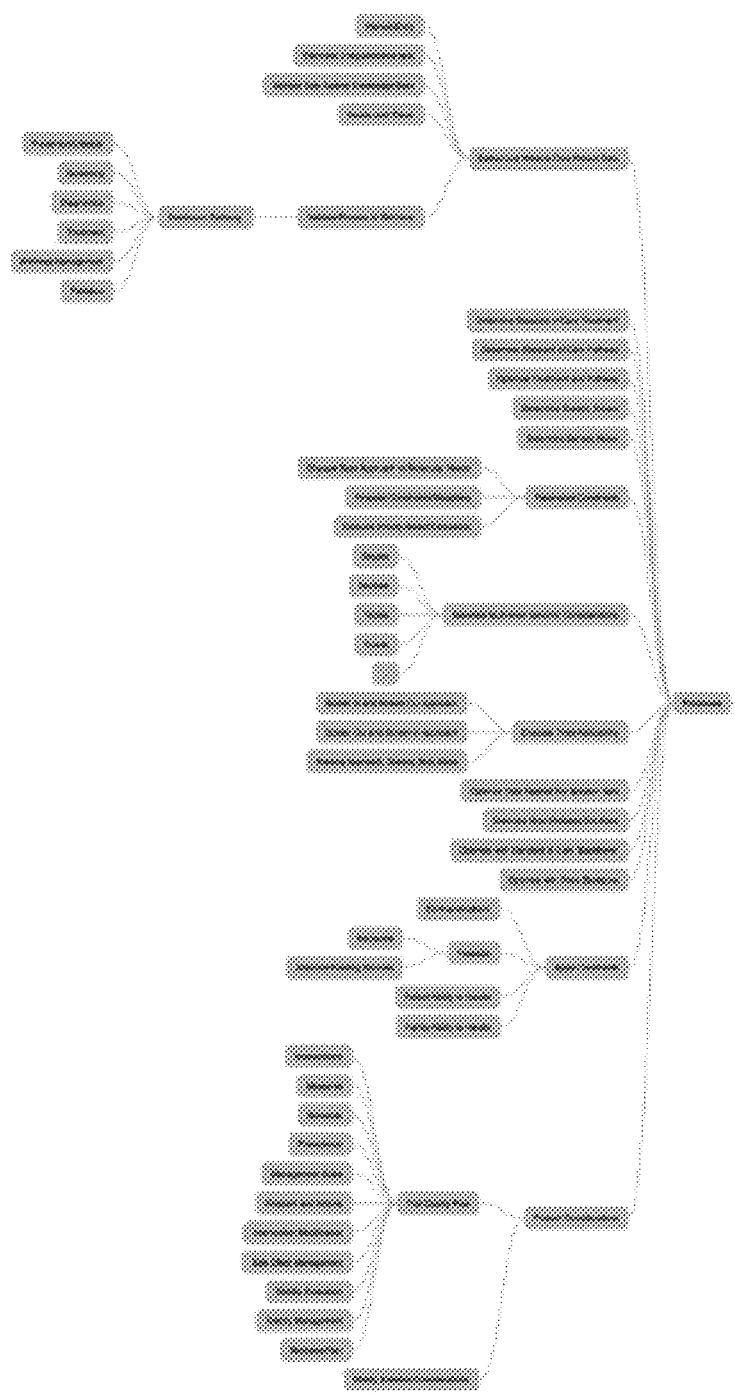
FIG. 4 is an exemplary model illustrating the relationship between various processes of a system described herein.

With regard to FIG. 4, and by way of example, it is contemplated that a system and associated methods may provide an automated process operative to perform data sourcing that may include gathering and validating core patient data (e.g., via CCD/CCDA XML files). The data may be sourced manually, electronically, or a combination thereof, through electronic integrations/interfaces with electronic sources of truth for the patient. The data sourcing may also include further gathering and validation of core patient data, as requested/required by the system (e.g., in response to identifying an individual data field required for evaluation of a rule) and associated methods upon determination according to rule blocks that additional critical data is needed in order to arrive at or to optimize a solution set (e.g., a personalized treatment plan) for the individual. The data sourcing may also include electronic integration/interface with other systems to obtain data needed to feed the knowledge base and facilitate reasoning. This may include iterative validation of provided data against the knowledge base, ensuring integrity of input (e.g., symptoms and interactions that are inconsistent with a diagnosis provided or consistent with another diagnosis).

The sourced knowledge, information, and data (e.g., patient structured data, patient genetic mutation data, treatment plan alternative data, etc.) can then be validated by validation of the process that should have taken place in order to arrive at the current state of the individual including validation across the continuum of care of the disease (e.g., in cancer, the continuum pathway includes prevention/lifestyle, disease screening based on stage of life, lifestyle and family history, diagnostic testing needed to confirm diagnosis and stage, including genomic tumor sequencing, treatment and supportive care options based on, and tailored to, the unique circumstance of each patient, and palliation and/or wellness follow-up care pathways/regimens).

In turn, the system may generate a personalized treatment plan by determining the standard of care pathway for the individual (e.g., diagnostic tests, treatment alternatives, supportive care and wellness follow-up for a newly screened individual with a positive mammogram) and optimizing the treatment and overall care pathway based on knowledge of combined therapies and attributes of the individual (e.g., performance status, allergies, other existing health conditions, prior therapies). Furthermore, the personalized treatment plan may be generated by determining the genetic drivers of the specific disease and isolating genetic "noise", that is those alterations that are not driving the disease or pose no threat or contraindication to possible therapies. The plan generation may include rationalizing constraints of alternative therapeutic approaches utilizing rule blocks with due consideration to at least a disease-based approach (breast cancer treatments) versus molecular/genetic approaches (e.g., treat ALK mutation and BRCA1 and BRCA2 markers), financial constraints/weighting to present all viable options and select a treatment which is fiscally viable for the individual (ability/willingness to pay), and evaluation of priority based exclusions (e.g., exclude an approach that would fully compromise a cancer patient that, for example, has Lupus).

Generation of the personalized plan data may include generating multi-level genomic considerations by combining drug regimens based on hitting most if not all genetic drivers indicated in patient genetic mutation data from the onset of treatment. This results in multiple drug combinations (doubles, triples, quads, etc.) depending upon the number of driver mutations and the numerous other constraints/contraindications for the therapies once combined. Applicability of clinical trials may be evaluated by both screening in and screening out trials that are relevant to an individual's attributes as indicated by patient structured data and patent genetic mutation data (e.g., as evaluated by application of rules by the inference engine). This may be done in multiple ways to increase efficiency and find the most probable helpful trials, specifically using approaches where, individuals are screened into trials that they may be eligible for based on an optimized set of data as determined by the engine through knowledge extraction. The individual may then be subsequently screened out of the trial based on further unique data characteristics and enrollment criteria for the specific trial (those that are not screened out may become viable candidates for treatment or modification of more innovative approaches using the clinical trial as a therapeutic backbone). In addition, clinical trials may be evaluated by a screen out and screen in approach which does the same as above except in the reverse order and proceeding based on the most efficient and effective direction as determined by the inference engine. Further still, a "rocking" approach (screen in/out then screen out/in) may be used where the engine determines the optimal direction and duration before reversing direction and changing duration.

The generation of the personalized treatment plan may include optimizing the data needed for solution sets that are viable (e.g., if only three solutions are viable and each requires an M and an X, confirm M and X first). Additionally, the generation of the personalized treatment plan may include generating the most probable solutions for inclusion in a personalized treatment plan by applying knowledge rules of thumb extracted from successful practice (e.g., where an individual suffering from a cancer has failed four or more lines of therapy, and had a 43% remission rate when standard of care expects 1% and the therapy used was a triple drug therapy in advance of surgery). Further optimization of the personalized treatment plan may include optimizing with standard of care as the "backbone" to add/alter the best-known standard to include genomic based targeted treatments and immunotherapies, optimizing the trials backbone in the same manner as standard of care therapies, except substituting the clinical trial as the backbone upon which genomic based therapies will be added. Further still, the generation may include applying contraindications such as financial reality and ability to fund therapy, regardless of source (insurance, compassionate drug, individual's personal finances, etc.), individual's ability to tolerate the therapy, and family's ability to tolerate the impact of the therapy.

As described above, once the personalized treatment plan has been generated, the system may present therapy considerations in a cohesive, clear, clinical trial quality manner including specification of relevant details pertaining to, for example, interventions, measures, schedule, precedence, management rules (including test interpretation, escalation, dose modification, etc.), endpoints and actions to be taken when reached (e.g., when to stop therapy and go to next option), intervention modification (therapy escalation, reduction, omission, delays, etc.), side effect management including recognition, severity assessment and remedial actions, toxicity evaluation and management, reporting (individual status, outcomes), wellness plan components and actions assuming treatment success, and modifying chosen baseline therapy considerations and action in the clinic after physician approval.

With reference to FIG. 17, an embodiment of a system 100 for use in generation of a personalized treatment plan is depicted. The system 100 may include a data ingestion engine 110, an inference engine 120, and a patient/provider interface 130. As may be appreciated, the data ingestion engine 110 and/or inference engine 120 may include one or more processors and/or physical memories that may store and execute instructions for providing the functionality described herein.

The data ingestion engine 110 may be in operative communication with a plurality of sources 102a-102n of information regarding an individual. As described above, the sources 102a-102n may correspond to manually input data, digital data files, or other appropriate formats of information. In any regard, the data ingestion engine 110 may be operative to receive, inspect, validate, parse, and store patient data in a data structure in a database 112.

Figure 5:
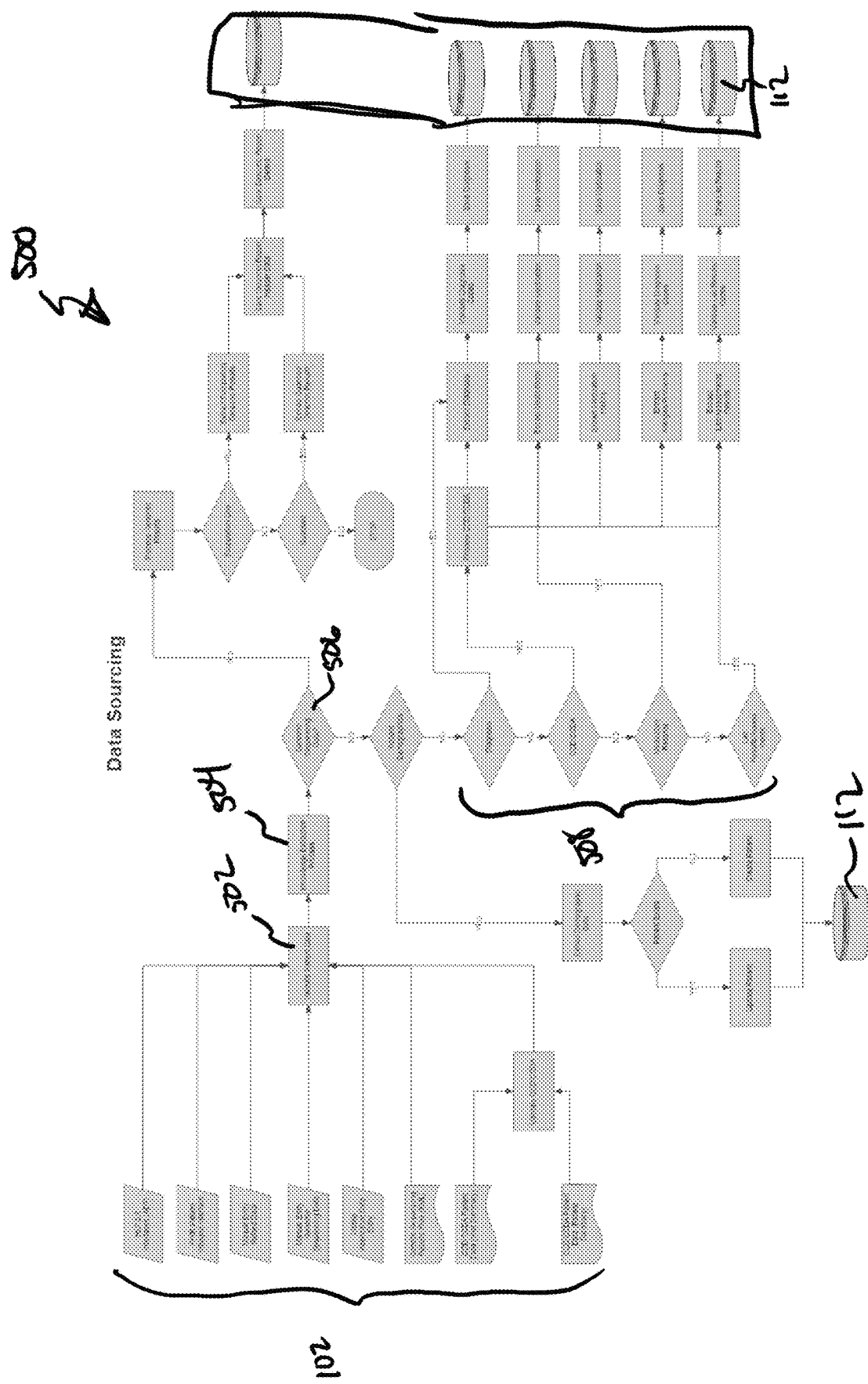
FIG. 5 is a flow diagram illustrating a data acquisition process.
Figure 6:
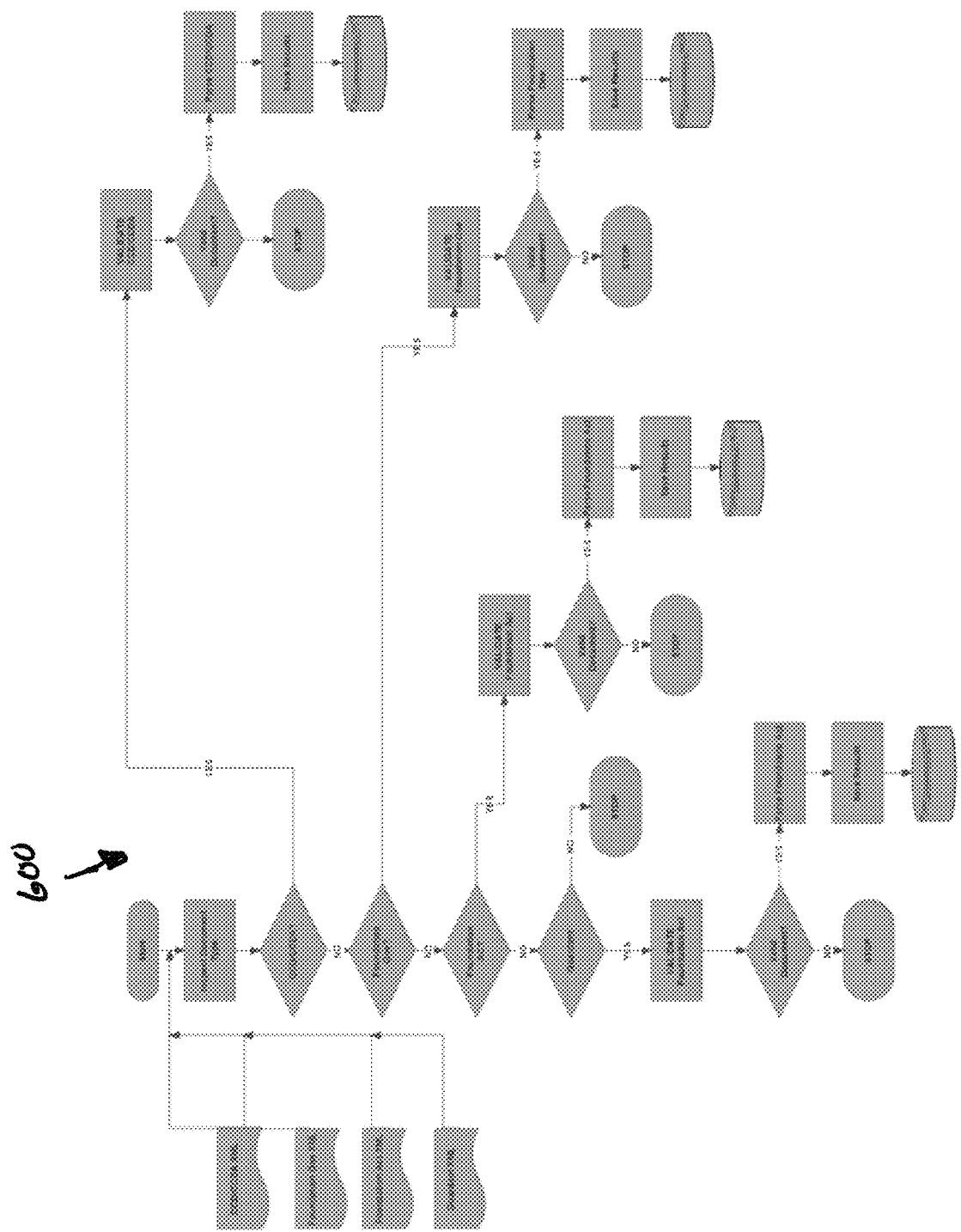
FIG. 6 is a flow diagram illustrating a processing overview of healthcare data document acquisition, parsing, and storage.

With reference to FIG. 5, a schematic representation of a method 500 for operation of the data ingestion engine 110 is depicted. As may be appreciated, a plurality of data sources 102 may be provided. Thereafter the patient data may be validated 502 and a knowledge extraction process may be applied at 504. This may include extracting genetic data from the patient information 506. Based on the respective type of data source, specific data may be extracted at 508 from the various data sources 102 and eventually stored in the database 112. In this regard, FIG. 5 represents a method that may be utilized to extract patient data for storage in a data structure in a database 112. In relation to the extraction of genetic data at 506, FIG. 6 depicts a further process 600 that may be specifically utilized for extraction of genetic data from one or more the sources 102.

In any regard, it may be appreciated that the database 112 may store the patient data in a data structure. Specifically, the original source information retrieved from the source 102 may be stored in the database 112 in its entirety. Moreover, the individually extracted or parsed data from the sources 102 may be stored in individual data fields. These individual data fields may describe information about the individual in more granularity than that of the original source 102. Each of the individual data fields may be individually indexed such that the individual data fields may be specifically accessed (e.g., by the inference engine 120 as described in greater detail below). As may be appreciated, this may allow for granularity in retrieving specific patient data corresponding to data presented in a single given individual data field for use in the system 100. FIGS. 1-4 may represent hierarchically arranged individual data portions that may correspond to a data structure stored in the database 112 to be populated with patient data. That is, any one of the nodes depicted in FIGS. 1-4 may correspond to a respective individual data portion that may be populated with information about an individual by populating parsed data with respect thereto. It may be appreciated that not all individual data fields may populated for each individual based on the various sources that may be provided with respect to the individual. In this regard, in at least some of the individual data fields represented in FIGS. 1-4, no corresponding patient data may be provided.

Figure 12:
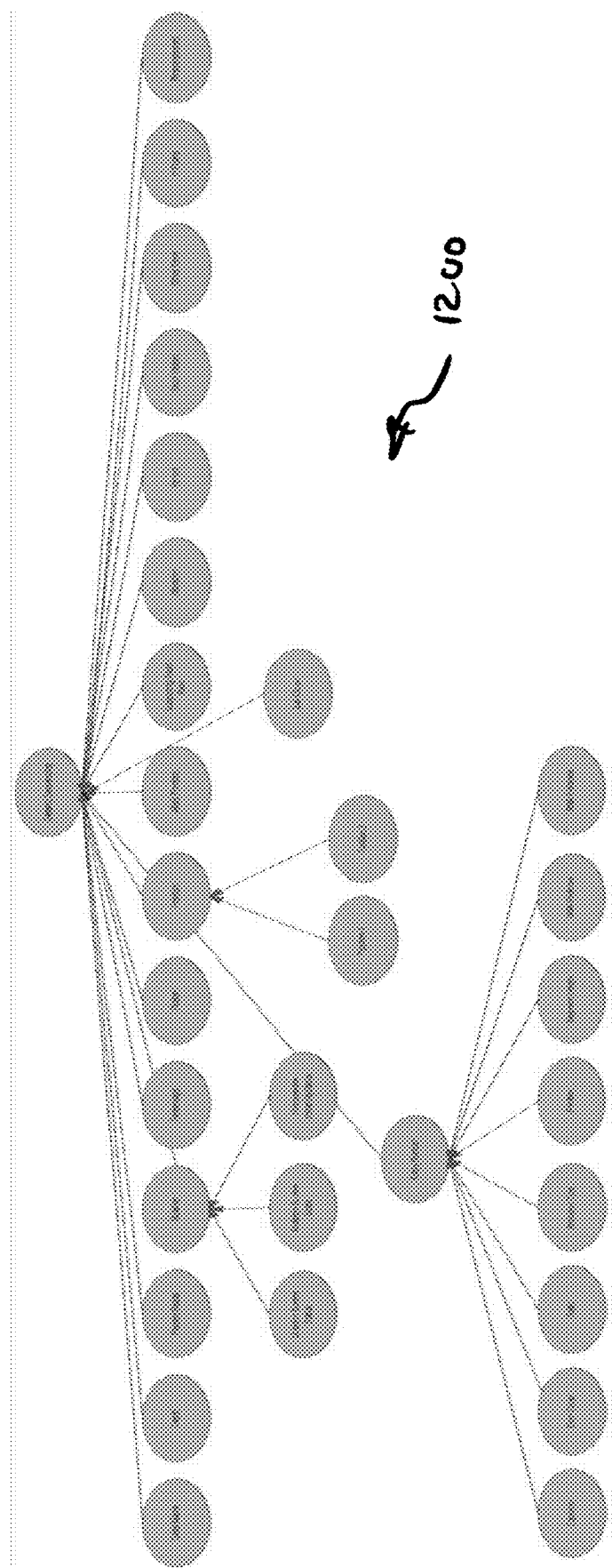
FIG. 12 is an exemplary hierarchical data structure designed for storing individual patient genetic sequencing details.

With specific reference to patient genetic data, a hierarchical data structure 1200 is depicted in FIG. 12 that may be utilized for storage of genetic patient data. That is, each node in FIG. 12 may represent an individual genetic data portion that may be populated by way of parsed genetic data (e.g., using process 600 depicted in FIG. 6). As may be appreciated, the hierarchical data structure 1200 depicted in FIG. 12 may comprise a portion of the patient data stored in the database 112. That is, reference to individual data fields or patient data may include genetic patient data including individual genetic data portions described in FIG. 12.

With returned reference to FIG. 17, the inference engine 120 may be in operative communication with the data ingestion engine 110, and specifically the database 112. While the database 112 is shown as being a part of the ingestion engine 110, it may be appreciated that the database 112 *a* provided remotely from the data ingestion engine 110 such that the data ingestion engine 110 may populate the database 112, yet not be physically associated with the database 112.

Figure 13:
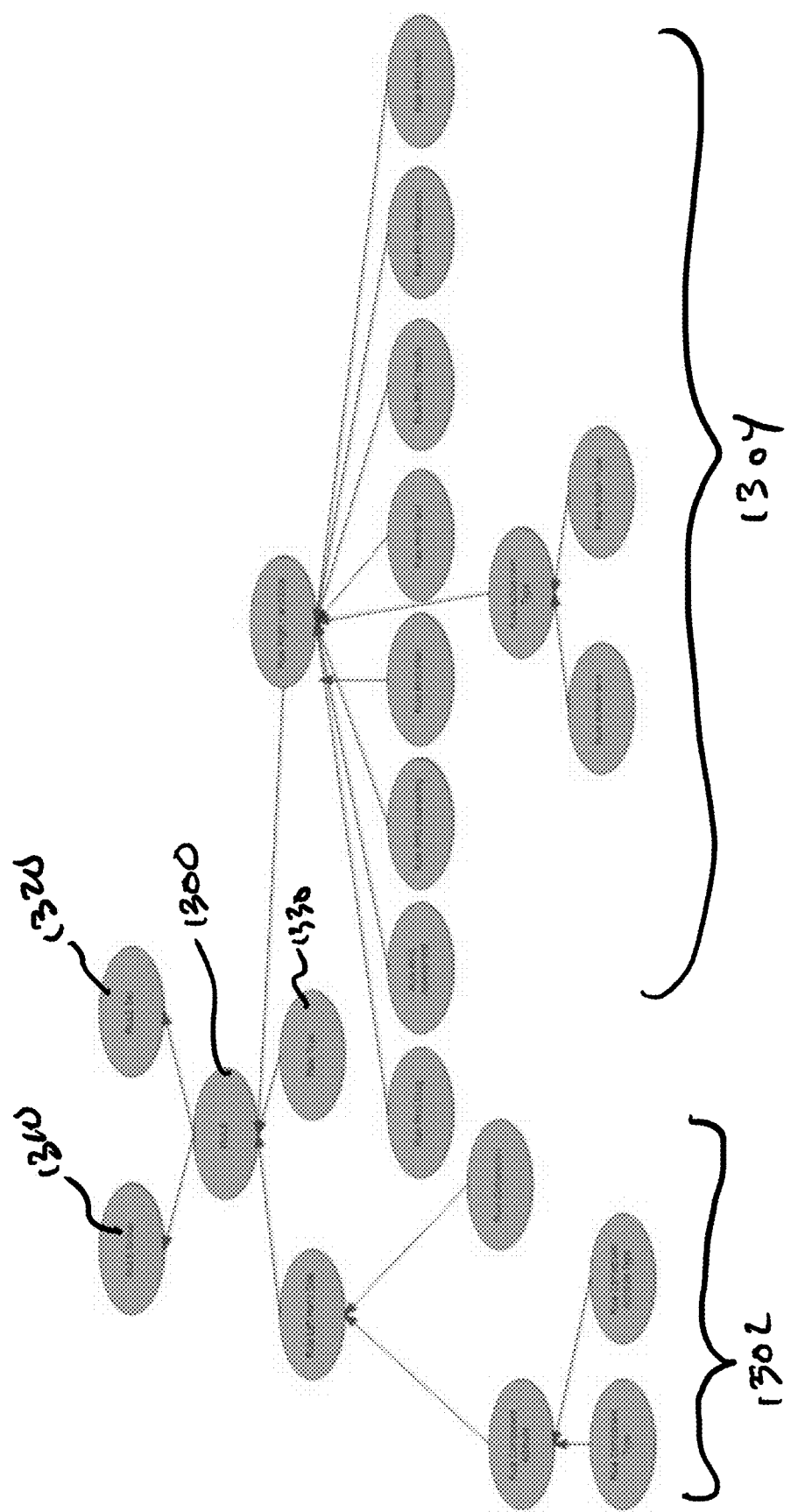
FIG. 13 is an exemplary data structure for inference engine rule blocks.

In any regard, the inference engine 120 may be operative to access the database 112 to retrieve portions of the patient data stored therein in the data structure. In addition, the inference engine 120 may be in operative communication with a rules database 122. The rules database 122 may store one or more rule sets that may be comprised of rule blocks. A schematic representation of a rule block 1300 is shown in FIG. 13. The rule block 1300 may have rule descriptors 1310, 1320, and 1330 that may include categorization other characterizations of the rule block 1300 for use in organizing the rules database 122.

In addition, the rule block 1300 may comprise a conditional component 1302 and an action component 1304. The conditional component 1302 (also referred to as the rule left-hand side) may include rule component attributes including rule component types and rule component attribute types that may correspond to individual data fields of the patient data. In addition, the conditional components 1302 may include a rule conjunction as described above that may be utilized to generate an executable expression that is conditional upon, and evaluated in relation to, one or more individual data fields of the data structure comprising information about the individual as stored in the database 112. That is, each rule block 1300 may have in the conditional component 1302 attributes that correspond to specific ones of the individual data fields of the patient data in the data structure.

In addition, the rule block 1300 may include an action component 1304 (also referred to as the rule right-hand side). As may be appreciated, the rule action component 1304 may describe a number of outcomes of the execution or evaluation of the rule in relation to the conditional component 1302. That is, the action component 1304 may dictate an action that may include inclusion of various instances or items in a personalized treatment plan and/or presentation of suggestions of instances or items for inclusion in a personalized treatment plan. Further still, the action component 1304 of the rule block 1300 may dictate further rules to be retrieved and evaluated in relation to the patient data in the database 112.

Figure 15:
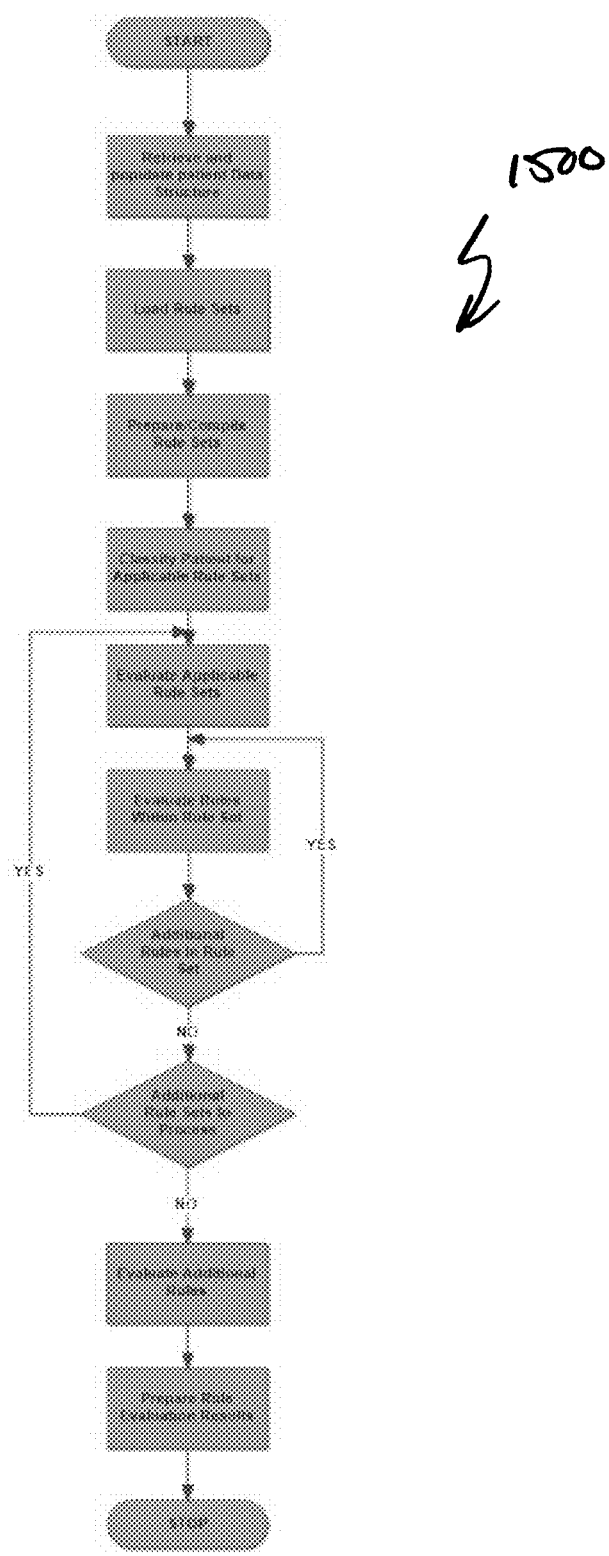
FIG. 15 is a flow diagram illustrating inference engine processing.

For instance, with further reference to FIG. 15, a method 1500 that describes operation of the inference engine 120 is shown. The method 1500 generally includes retrieval and population of patient data from the data structure. Furthermore, the method may include loading rule sets. As may be appreciated, the loading of the rule sets may include retrieval of rule sets and/or rule blocks from the rule database 122 that include attributes corresponding to individual data fields present in the patient data of the database 112 for a given individual. That is, any rule that implicates patient data present in the individual data fields for a given individual may be retrieved for processing by the inference engine 120. This may implicate the discussion above in which missing patient data may be identified and queries for completion of all the rules that are retrieved.

The method may also include preparing and compiling rule sets. The method may further include classifying the patient for applicable rule sets. Further still, the rules may be evaluated in an iterative process such that each rule is evaluated until there are no additional rules in the rule sets be completed. Thereafter, it may be determined whether additional rule sets need to be retrieved (e.g., based on action components 1304 of previously executed rules). If so, these additional rules are evaluated. Finally, the inference engine 120 may prepare rule evaluation results that may include generation of a personalized treatment plan or generation of suggestions for inclusion in a personalized treatment plan.

Figure 16:
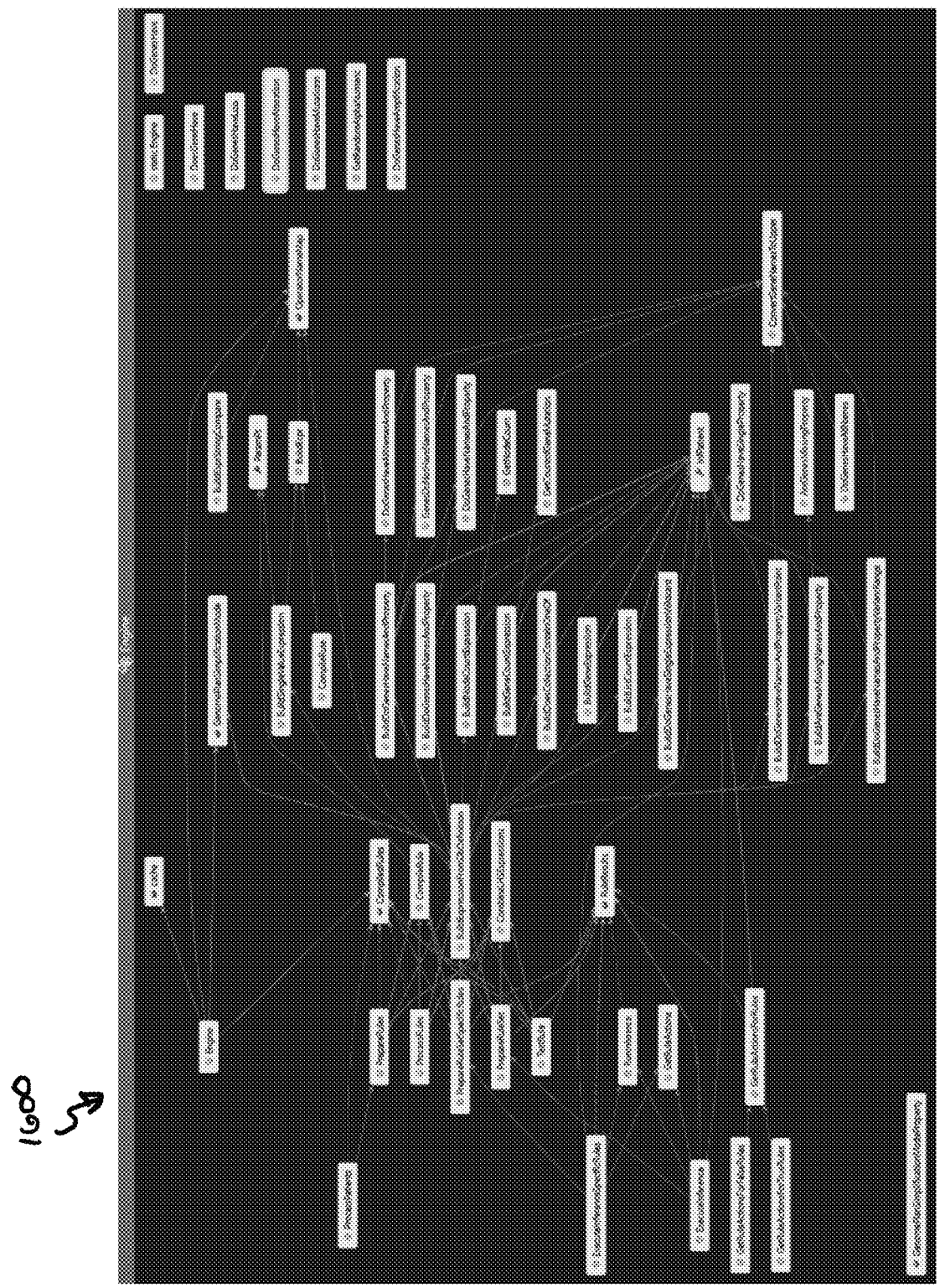
FIG. 16 is a detailed flow diagram illustrating inference engine processes.

As may be appreciated, the retrieval and execution of rule blocks 1300 from the rules database 122 may result in the retrieval and execution of a plurality of rules that may have dependent operation in relation to one another. This operation is schematically depicted at 1600 in FIG. 16. In this regard, each node in FIG. 16 may represent a given rule that may be linked to other rules by way of action components 1304 or as conditional components 1302 of given rules. Further still, the schematic 1600 may depict correlations or connections to data sources.

Figure 14:
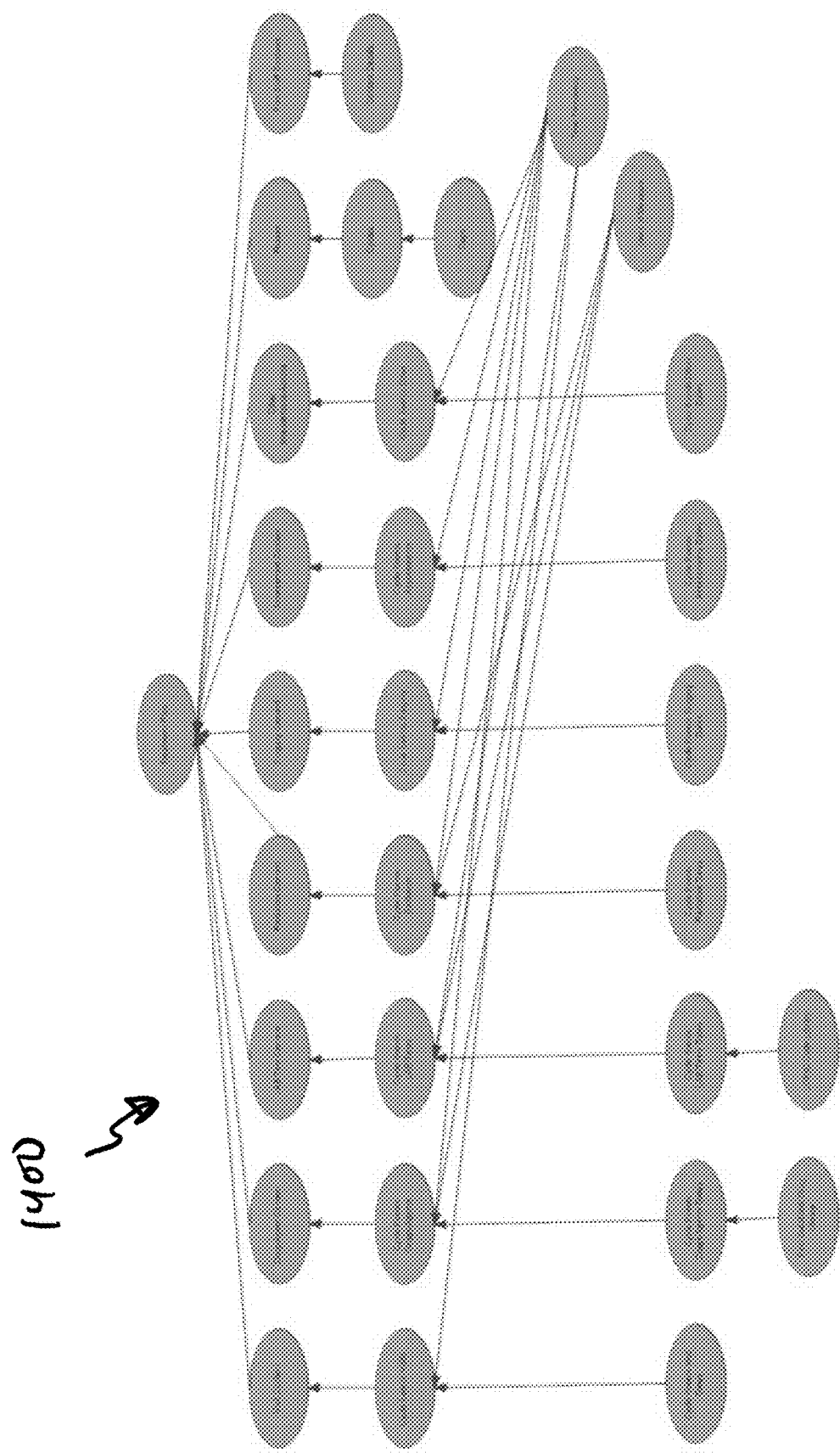
FIG. 14 is an exemplary data structure for storage of treatment plan details.

In this regard, the inference engine 120 may, in at least some embodiments, result in generation of a personalized treatment plan. A representation of a data structure 1400 for storage of treatment plan alternative data is depicted in FIG. 14. In this regard, various ones of the nodes depicted in FIG. 14 in relation to the data structure 1400 may be populated by operation of the inference engine 120 by execution of rules 1300 from the rule database 122 as executed in relation to patient data stored in the database 112.

Figure 11:
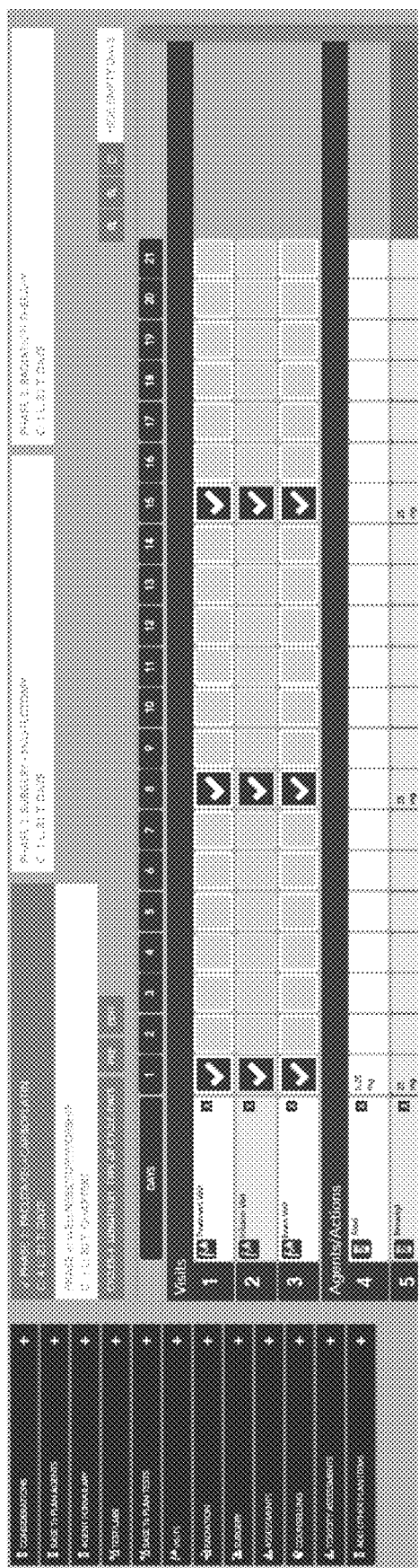
FIG. 11 illustrates an embodiment of a graphical user interface for treatment plan creation.

With returned reference to FIG. 17, a patient/provider interface 130 may be provided that is in operative communication with the inference engine 120. The patient/provider interface 130 may be operative to access the data structure 1400 representing the personalized treatment plan for use in generation of outputs corresponding to the personalized treatment plan. For instance, FIG. 11 depicts a graphical user interface 1100 that may correspond to a representation of treatment plan alternative data as displayed by the patient/provider interface 130. In this regard, the graphical user interface 1100 may include individual grid cells that represent scheduling of a given item within the confines of a personalized treatment plan in relation to a temporal aspect. That is, each cell in the grid may represent a given temporal period that may include, for example, a treatment plan phase, treatment plan cycle, or treatment plan day. The personalized treatment plan may be pre-populated with items from the personalized treatment plan as determined by operation of the inference engine 120. Further still, suggestions of items for inclusion in the treatment plan may be presented that may be added to the treatment plan by interfacing with the graphical user interface 1100. In addition, individual rows of the grid depicted in FIG. 11 may be edited by selection of an item within the screen (e.g., by dragging and dropping, clicking, or other interaction). This may include scheduling or unscheduling an item or providing further details or information regarding the item including, for example, details regarding a procedure, specific dosages, or other particular information for the given item selected.

As described above, interfacing with the graphical user interface 1100 may include editing the personalized treatment plan. In this regard, as changes are made the plan, real time checking may be applied that may, for example, check for real-time drug interaction or may otherwise flag a user of any potential hazards related to the edits made to the plan. Furthermore, inclusion of certain items in the plan may result in automatic triggering of other items for inclusion the plan. For example, as drug interventions are added to the plan, monitoring tests and/or toxicity assessments may be identified and/or automatically added the plan in response to the addition of the drug intervention. This may be as a result of triggering a new rule by virtue of adding an item to the plan which is represented in FIG. 17 in relation to the feedback loop between the patient/provider interface 130 and the inference engine 120. Furthermore, as shown in FIG. 17, the ingestion engine 110 may provide feedback directly to the patient/provider interface 130 such that changes in information about the individual received from data sources 102 to be fed into the patient/provider interface 130 for inclusion in the personalized treatment plan.

Figure 7:
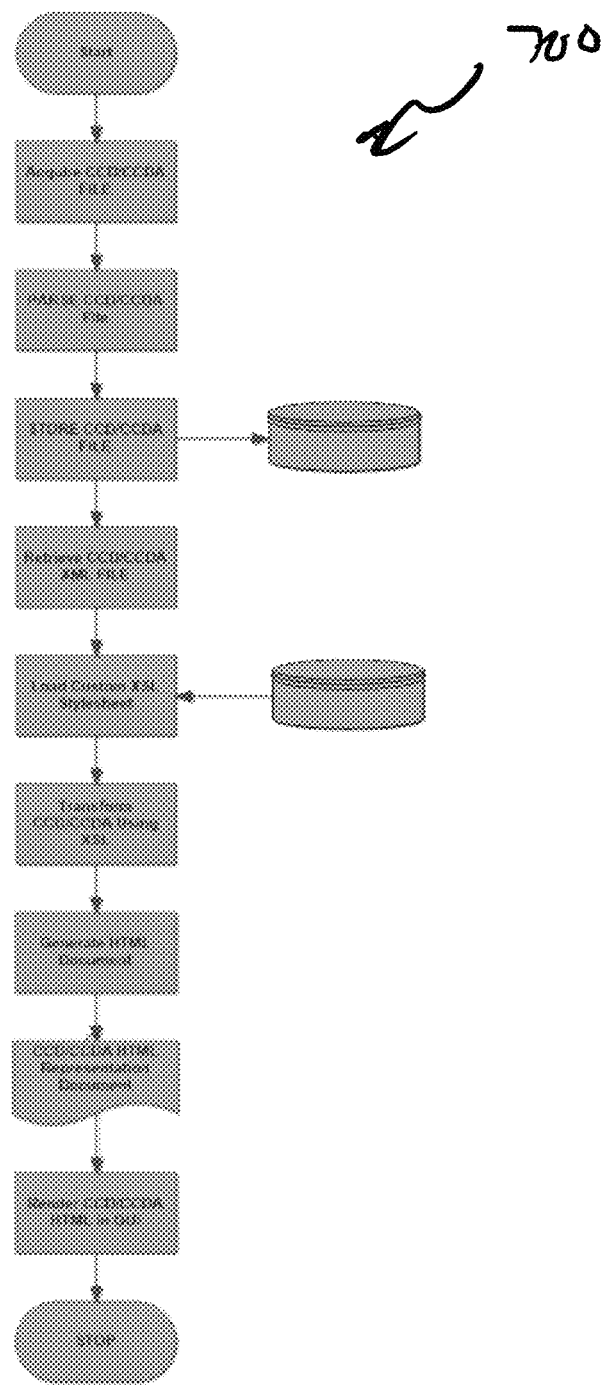
FIG. 7 is a flow diagram illustrating a processing overview of CCD data acquisition and XML to HTML transformation and rendering.
Figure 9:
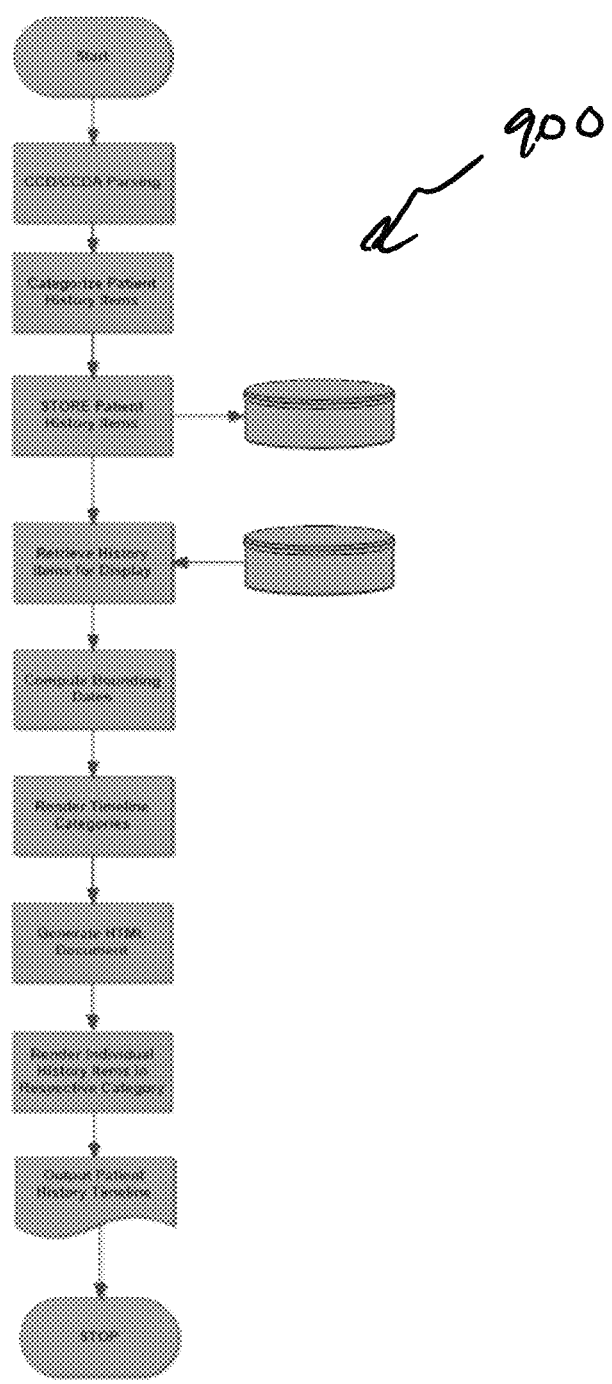
FIG. 9 is a flow diagram illustrating a processing overview of history item data acquisition and rendering.
Figure 10:
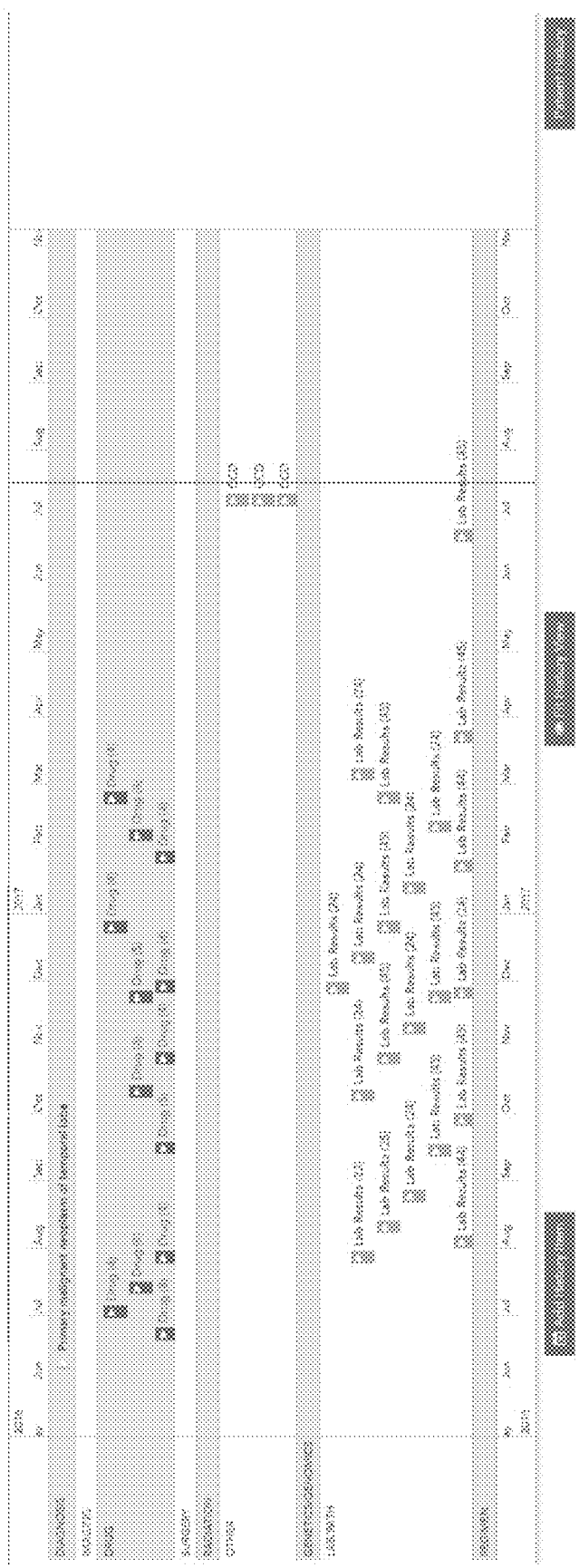
FIG. 10 illustrates an embodiment of a timeline graphical user interface.

Furthermore, information received, parsed, or extracted from the ingestion engine 110 may be provided directly to the patient/provider interface 130 for display of patient data by way of the patient/provider interface 130. For example, FIG. 7 depicts a process 700 by which information from a data source may be formatted by application of an XSL stylesheet for rendering a graphical user interface 800 that may display various patient data including individual data fields stored in the database 112. Furthermore, FIG. 9 depicts a method 900 whereby information from the database 112 may be retrieved and used to generate a timeline 1000 as depicted in FIG. 10. As may be appreciated in FIG. 10, timeline 1000 may depict patient data from the database 112 and/or may include items from a patient treat plan. The timeline may include discrete categorical portions into which different corresponding ones of individual data fields may be mapped for display. In this regard, instances may be populated in the timeline and organized based on a category as depicted in FIG. 10. In this regard, the different categories shown in FIG. 10 may include diagnosis, imaging, drugs, surgeries, radiation, genetics or genomics, laboratory or pathology results, or other regimens, instances of any of which may be displayed in the corresponding categorical portion of the timeline 1000. The instances in the timeline 1000 may be directly editable by selecting the instance to provide or modify data associated therewith. Furthermore, the timeline may be bounded by one or more bounding dates including, for example an upper or lower bounding date for selective inclusion of certain instances from the patient data or personalized treatment plan. The bounding dates may be selectable by a user and modifiable for viewing different time portions. In this regard, the timeline 1000 may display both patient data and/or information related to the personalized treatment plan.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method executed by a hardware processor of a computing system for generating one or more personalized treatment plan for customized healthcare treatment for an individual suffering from at least one medical condition, the method comprising:

receiving, at the computing system, information about the individual from one or more sources, wherein the information about the individual is at least sourced from genetic data regarding the individual comprising a proprietary third party formatted file with discrete data pertaining to the genetic data of the individual and received as a digital data file;

extracting, using the hardware processor, patient data from the received information and storing the extracted patient data in a memory of the computing system in a data structure including the genetic data regarding the individual being parsed to populate a hierarchical data structure stored in the patient data, wherein the genetic data regarding the individual are stored both as a complete file and parsed individual genetic data portions comprising less than the complete file, and wherein the individual genetic data portions are individually indexed in the hierarchical data structure for evaluation; and utilizing the patient data in the data structure to generate, by the hardware processor, the one or more personalized treatment plan for the individual, the one or more personalized treatment plan being automatically updated over time, optimizing the individual's treatment outcome, wherein the generation of the one or more personalized treatment plan comprise application of rules to the hierarchical data structure by an inferencing engine executed by the hardware processor, wherein the rules are stored in a rule data structure that is accessible by the inferencing engine, wherein the data structure comprises individual data fields populated with parsed data from the individual genetic data portions from the hierarchical data structure about the individual that are individually accessible by the inferencing engine, and wherein the inferencing engine is operative to query the individual data fields from the structured format for application to one or more rules.

2. The method of claim 1, wherein the information about the individual is further sourced from one or more of a patient summary clinical document, manual data entry, or a Health Level 7 (HL7) interface.

3. The method of claim 2, wherein the one or more sources comprises the patient summary clinical document that comprises an extensible markup language (XML) document containing the information about the individual, and wherein the XML document comprises one of a continuity of care document (CCD) or a clinical document architecture (CDA) document.

4. The method of claim 1, wherein the information about the individual from the one or more sources is validated prior to the extracting, wherein the validation is based on the document type, wherein the extracting comprises parsing data from the information about the individual and the data structure comprises the parsed data in the data structure that is stored in a database, wherein the data structure comprises bulk input data comprising the information about the individual and individual data fields corresponding to the parsed data, and wherein the individual data fields are individually indexed for direct access in the database.

5. The method of claim 4, wherein the parsed data in the data structure is rendered into a human readable output, wherein the human readable output is generated by application of an extensible stylesheet language (XSL) stylesheet to the structured format, and wherein the XSL stylesheet comprises instructions for the manner in which each individual data field is rendered in the human readable output.

6. The method of claim 5, wherein the human readable output comprises a timeline that includes instances corresponding to parsed data in the individual data fields of the data structure, wherein the timeline comprises discrete categorical portions into which different corresponding ones of the individual data fields are mapped for display of the instances in a corresponding discrete categorical portion of the timeline, and wherein the discrete categorical portions of the timeline correspond to categories including one or more of diagnosis, imaging, drug, surgery, radiation, genetics/genomics, laboratory/pathology results, or regimen.

7. The method of claim 1, wherein the inferencing engine retrieves one or more rules from the rule data structure and assembles the rules into executable expressions for evaluation by a clinical team in real time in relation to one or more individual data fields of the data structure corresponding to the information about the individual, and wherein the one or more rules are selected for retrieval from the rule data structure based upon one or more rule attributes associated with each rule corresponding to an individual data field identified within the data structure.

8. The method of claim 7, wherein every rule from the rule data structure is retrieved that comprises a rule attribute corresponding to an individual data field populated with one or more of the individual genetic data portions from the information regarding the individual, wherein the rules comprise one or more condition components and one or more action components, wherein the condition components are conditional on, and evaluated in relation to, one or more individual data fields of the data structure comprising the individual genetic data portions and other clinical and demographic data about the individual, and wherein the condition components and action components of the rules comprises executable expressions that are conditional on, and evaluated in relation to, the one or more individual data fields of the data structure comprising the individual genetic data portions and other clinical and demographic data portions about the individual.

9. The method of claim 8, wherein execution of the one or more rules results in attributes of the personalized treatment plan.

10. The method of claim 8, wherein execution of the one or more rules results in suggestions for the personalized treatment plan that are presented in relation to an output of the personalized treatment plan presented to a user.

11. The method of claim 7, wherein the inferencing engine is operative to determine one or more individual data fields required for evaluation of an executable expression that is not present for a retrieved rule.

12. The method of claim 11, wherein a query for the one or more individual fields required for evaluation of the executable expression is generated in response to the determination.

13. The method of claim 1, wherein the personalized treatment plan is stored as a structured plan data file, and wherein the structured plan data file comprises plan data fields corresponding to different respective elements of the personalized treatment plan.

14. The method of claim 13, wherein the elements comprise one or more of drugs, laboratory evaluations, tests, assessments, radiation, medical provider visits, and surgical operations.

15. The method of claim 14, wherein individual ones of the elements are stored in the plan data fields based on respective external lexicon corresponding to the respective element.

16. The method of claim 15, wherein the respective external lexicon comprises one or more of logical observation identifiers names and codes (LOINC), common terminology criteria for adverse events (CTCAE) grading schemes, national drug code (NDC) identifier information, systematized nomenclature of medicine (SNOMED) codes, and international classification of diseases (ICD) 10 codes.

17. The method of claim 13, wherein the plan fields are each cross referenced against a temporal descriptor.

* * * * *